US012559733B2

(12) United States Patent
McInnes et al.

(10) Patent No.: US 12,559,733 B2
(45) **Date of Patent: *Feb. 24, 2026**

(54) OPTIMIZATION OF TYPE IV BRAF INHIBITORS FOR THE TREATMENT OF MELANOMA

(71) Applicant: UNIVERSITY OF SOUTH CAROLINA, Columbia, SC (US)

(72) Inventors: Campbell McInnes, Irmo, SC (US); Chad Beneker, Columbia, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 160 days.

This patent is subject to a terminal disclaimer.

(21) Appl. No.: 17/409,306

(22) Filed: Aug. 23, 2021

(65) Prior Publication Data

US 2022/0127585 A1 Apr. 28, 2022

Related U.S. Application Data

(60) Provisional application No. 63/104,268, filed on Oct. 22, 2020.

(51) Int. Cl.

| | |
|---|---|
| ***C12N 9/12*** | (2006.01) |
| ***A61K 38/00*** | (2006.01) |
| ***A61K 38/45*** | (2006.01) |
| ***A61P 35/00*** | (2006.01) |
| ***C07K 7/64*** | (2006.01) |

(52) U.S. Cl.

CPC ................ *C12N 9/12* (2013.01); *A61K 38/45* (2013.01); *A61P 35/00* (2018.01); *C07K 7/64* (2013.01); *C12Y 207/11001* (2013.01); *A61K 38/00* (2013.01)

(58) Field of Classification Search

CPC .......... C12N 9/12; A61K 38/45; A61K 38/00; C07K 7/64; C12Y 207/11001; A61P 35/00

See application file for complete search history.

(56) References Cited

U.S. PATENT DOCUMENTS

| | | | | |
|---|---|---|---|---|
| 7,291,601 | B1 | 11/2007 | Chae et al. | |
| 7,432,260 | B2 | 10/2008 | Wang et al. | |
| 7,449,544 | B2 | 11/2008 | Zheleva et al. | |
| 7,576,091 | B2 | 8/2009 | McInnes et al. | |
| 7,897,605 | B2 | 3/2011 | Wang et al. | |
| 8,566,072 | B2 | 10/2013 | McInnes et al. | |
| 9,175,357 | B2 | 11/2015 | McInnes et al. | |
| 9,328,139 | B2 | 5/2016 | McInnes et al. | |
| 9,376,465 | B2 | 6/2016 | McInnes et al. | |
| 9,982,015 | B2 | 5/2018 | McInnes et al. | |
| 10,067,131 | B2 | 9/2018 | McInnes et al. | |
| 11,162,083 | B2 * | 11/2021 | McInnes .................. | C07K 7/08 |
| 2003/0036628 | A1 | 2/2003 | Zheleva et al. | |
| 2003/0086929 | A1 | 5/2003 | Tso et al. | |
| 2003/0129656 | A1 | 7/2003 | Park et al. | |
| 2003/0171904 | A1 | 9/2003 | Lewis et al. | |
| 2003/0187220 | A1 | 10/2003 | Park et al. | |
| 2003/0225527 | A1 | 12/2003 | Antonvsamv et al. | |
| 2004/0176301 | A1 | 9/2004 | Zheleva et al. | |
| 2004/0229290 | A1 | 11/2004 | Hellinga et al. | |
| 2005/0192300 | A1 | 9/2005 | Wang et al. | |
| 2005/0196808 | A1 | 9/2005 | Yaffe et al. | |
| 2005/0264628 | A1 | 12/2005 | Raggatt | |
| 2006/0040997 | A1 | 2/2006 | McInnes et al. | |
| 2006/0281687 | A1 | 12/2006 | Andrews et al. | |
| 2006/0293245 | A1 | 12/2006 | Zheleva et al. | |
| 2008/0070843 | A1 | 3/2008 | Livnah et al. | |
| 2008/0132484 | A1 | 6/2008 | McInnes et al. | |
| 2008/0167385 | A1 | 7/2008 | Kontopidis et al. | |
| 2008/0287439 | A1 | 11/2008 | Wang et al. | |
| 2009/0215805 | A1 | 8/2009 | Wood et al. | |
| 2010/0004141 | A1 | 1/2010 | Khvorova et al. | |
| 2012/0202970 | A1 | 8/2012 | McInnes et al. | |
| 2013/0289240 | A1 | 10/2013 | McInnes et al. | |
| 2014/0296484 | A1 | 10/2014 | McInnes et al. | |
| 2014/0316107 | A1 | 10/2014 | McInnes et al. | |
| 2016/0011195 | A1 | 1/2016 | McInnes et al. | |

(Continued)

FOREIGN PATENT DOCUMENTS

| | | |
|---|---|---|
| GB | 2369823 | 6/2002 |
| WO | WO 2004/067000 | 8/2004 |

(Continued)

OTHER PUBLICATIONS

Verdine, et al. "Stapled peptides for intracellular drug targets" Meth. Enzymol. 503, pp. 3-33 (Year: 2012).*

Yudin, Chem. Sci., 2015, 6, 30-49, DOI: 10.1039/c4sc03089c. (Year: 2015).*

Sharma et al., N-methylation in amino acids and peptides: Scope and limitations, Biopolymers. 109: e23110. DOI: 10.1002/bip.23110. (Year: 2018).*

(Continued)

*Primary Examiner* — Sudhakar Katakam
*Assistant Examiner* — Zachary J Miknis
(74) *Attorney, Agent, or Firm* — DORITY & MANNING, P.A.

(57) ABSTRACT

Inhibitory peptides for modifying RAF kinase protein dimerization are described. The peptides display a binding affinity for the dimer interface of a B-Raf, allowing for modification of RAF kinase dimerization, and inhibition of tumor growth. An embodiment of the disclosure is a peptide generated by modifying SEQ ID NO: 1, which corresponds to amino acids 503-521 of B-Raf kinase, e.g., cyclization, N-terminal capping, C-terminal capping, substitution of one or more amino acid residues, etc. The peptides disclosed herein include a modification to SEQ ID NO: 1 that can improve or otherwise alter binding affinity of the peptide to the dimer interface.

19 Claims, 18 Drawing Sheets

Specification includes a Sequence Listing.

(56) References Cited

U.S. PATENT DOCUMENTS

2017/0218018 A1 8/2017 McInnes et al.
2017/0283445 A1 10/2017 McInnes et al.
2019/0382738 A1 12/2019 McInnes et al.

FOREIGN PATENT DOCUMENTS

WO WO 2005/005438 1/2005
WO WO 2005/040802 5/2005
WO WO 2005/042565 5/2005
WO WO 2005/052147 6/2005
WO WO 2005/108421 11/2005

OTHER PUBLICATIONS

Beneker, et al. "Design and Synthesis of Type IV Inhibitors of BRAF Kinase That Block Dimerization and Overcome Paradoxical MEK/ERK Activation" J. Med. Chem. 62 pp. 3886-3897. (Year: 2019).*
ACS. "Cancer Facts & Figures 2020" *Am. Cancer Soc.* (2020) pp. 1-74.
ACS. "Cancer Facts & Figures 2010" *Am. Cancer Soc.* (2010) pp. 1-68.
Agianian, et al. "Current Insights of BRAF Inhibitors in Cancer" *J. Med. Chem.* 61 (2018) pp. 5775-5793.
Ahlbach, et al. "Beyond Cyclosporine A: Conformation-Dependent Passive Membrane Permeabilities of Cyclic Peptide Natural Products" *Future Med. Chem.* 7 (2015) pp. 2121-2130.
Andrews, et al. "REPLACE: A strategy for iterative design of cyclin-binding groove inhibitors" *ChemBioChem* 7 (2006) pp. 1909-1915.
Beneker, et al. "Design and Synthesis of Type IV Inhibitors of BRAF Kinase That Block Dimerization and Overcome Paradoxical MEK/ERK Activation" *J. Med. Chem.* 62 (2019) pp. 3886-3897.
Bernal, et al. "Reactivation of the p53 tumor suppressor pathway by a stapled p53 peptide" *J. Am. Chem. Soc.* 129 (2007) pp. 2456-2457.
Bollag, et al. "Clinical efficacy of a RAF inhibitor needs broad target blockade in BRAF-mutant melanoma" *Nature* 467 (2010) pp. 596-599.
Brummer, et al. "RAF Kinase Dimerization: Implications for Drug Discovery and Clinical Outcomes" *Oncogene* 39 (2020) pp. 4155-4169.
Brummer, et al. "Inducible gene deletion reveals different roles for B-Raf and Raf-1 in B-cell antigen receptor signaling" *EMBO J.* 21 (2002) pp. 5611-5622.
Buku, et al. "Mast Cell Degranulating (MCD) Peptide Analogs with Reduced Ring Structure" *J. Prot. Chem.* 11 (1992) pp. 275-280.
CCP4. "The CCP4 suite: programs for protein crystallography" *Acta Crystallogr. D* 50 (1994) pp. 760-763. (Abstract only).
Chatterjee, et al. "N-methylation of peptides and proteins: An important element for modulating biological functions" *Angew Chem.* 52 (2013) pp. 254-269.
Chatterjee, et al. "Synthesis of N-methylated cyclic peptides" *Nat. Protoc.* 7 (2012) pp. 432-444.
Chmielecki, et al. "Comprehensive Genomic Profiling of Pancreatic Acinar Cell Carcinomas Identifies Recurrent RAF Fusions and Frequent Inactivation of DNA Repair Genes" *Cancer Discov.* 4(2014) pp. 1398-1405.
Chou, et al. "Prediction of β-turns" *Biophys. J.* 26 (1979) pp. 367-383.
CCP4. "The CCP4 suite: Programs for protein crystallography" *Acta Cryst.* D50 (1994) pp. 760-763.
Cox, et al. "The Raf inhibitor paradox: Unexpected consequences of targeted drugs" *Cancer Cell* 17 (2010) pp. 221-223.
Diedrich, et al. "Discrete cytosolic macromolecular BRAF complexes exhibit distinct activities and composition" *EMBO J.* 36 (2017) pp. 646-663.
Durrant, et al. "Targeting the Raf kinases in human cancer: The Raf dimer dilemma" *Br. J. Cancer* 118 (2018) pp. 3-8.
Eisenhardt, et al. "Phospho-proteomic analyses of B-Raf protein complexes reveal new regulatory principles" *Oncotarget* 7 (2016) pp. 26628-26652.
Evans, P.R. "Data reduction" *Proc. of CCP4 Daresbury Study Weekend* (1993) pp. 114-122.
Freeman, et al. "Effects of Raf dimerization and its inhibition on normal and disease-associated Raf signaling" *Mol. Cell* 49 (2013) pp. 751-758.
Ganz, T. "Defensins: Antimicrobial Peptides of Innate Immunity" *Immunology* 3 (2003) pp. 710-720.
Garnett, et al. "Guilty as charged: B-RAF is a human oncogene" *Cancer Cell* 6 (2004) pp. 313-319.
Giordanetto, et al. "Macrocyclic drugs and clinical candidates: What can medicinal chemists learn from their properties?" *J. Med. Chem.* 57 (2014) pp. 278-295.
Haigis, et al. "Differential effects of oncogenic K-Ras and N-Ras on proliferation, differentiation and tumor progression in the colon" *Nat. Genet.* 40 (2008) pp. 600-608.
Hatzivassiliou, et al. "RAF inhibitors prime wild-type RAF to activate the MAPK pathway and enhance growth" *Nature* 464 (2010) pp. 431-435.
Haug, et al. "Metadherin exon 11 skipping variant enhances metastatic spread of ovarian cancer" *Int'l J. Cancer* 136 (2015) pp. 2328-2340.
Heidorn, et al. "Kinase-dead BRAF and oncogenic RAS cooperate to drive tumor progression through CRAF" *Cell* 140 (2010) pp. 209-221.
Herr, et al. "B-Raf Inhibitors Induce Epithelial Differentiation in BRAF-Mutant Colorectal Cancer Cells" *Cancer Res.* 75 (2015) pp. 216-229.
Herr, et al. "A novel MCF-10A line allowing conditional oncogene expression in 3D culture" *Cell Commun. Signal* 9:17 (2011) pp. 1-13.
Hingorani, et al. "$Trp53^{R172H}$ and $Kras^{G12D}$ cooperate to promote chromosomal instability and widely metastatic pancreatic ductal adenocarcinoma in mice" *Cancer Cell* 7 (2005) pp. 469-483.
Hu, et al. "Allosteric Activation of Functionally Asymmetric RAF Kinase Dimers" *Cell* 154 (2013) pp. 1036-1046.
Jemal, et al. "Cancer Statistics, 2010" *CA Cancer J. Clin.* 60 (2010) pp. 277-300.
Kamata, et al. "BRAF inactivation drives aneuploidy by deregulating CRAF" *Cancer Res.* 70 (2010) pp. 8475-8486.
Kaplan, et al. "Hyperactivation of MEK-ERK1/2 signaling and resistance to apoptosis induced by the oncogenic B-RAF inhibitor, PLX4720, in mutant N-RAS melanoma cells" *Oncogene* 30 (2011) pp. 366-371.
Karoulia, et al. "An Integrated Model of RAF Inhibitor Action Predicts Inhibitor Activity against Oncogenic BRAF Signaling" *Cancer Cell* 30 (2016) pp. 485-498.
Köhler, et al. "Activation loop phosphorylation regulates B-Raf in vivo and transformation by B-Raf mutants" *EMBO J.* 35 (2016) pp. 143-161.
Kontopidis, et al. "Truncation and optimisation of peptide inhibitors of cyclin-dependent kinase 2-cyclin a through structure-guided design" *ChemMedChem* 4 (2009) pp. 1120-1128.
Kontopidis, et al. "Differential binding of inhibitors to active and inactive CDK2 provides insights for drug design" *Chem. Biol.* 13 (2006) pp. 201-211.
Kordes, et al. "Cooperation of $BRAF^{F595L}$ and mutant HRAS in histiocytic sarcoma provides new insights into oncogenic BRAF signaling" *Leukemia* 30 (2016) pp. 937-946.
Lakowicz, J.R. "Principles of Fluorescence Spectroscopy" *Springer* (2006) pp. 1-959.
Lavoie, et al. "Regulation of RAF protein kinases in ERK signaling" *Mol. Cell Biol.* 16 (2015) pp. 281-298.
Lavoie, et al. "Inhibitors that stabilize a closed RAF kinase domain conformation induce dimerization" *Nat. Chem. Biol.* 9 (2013) pp. 428-436.
Leslie, A.G.W. "Recent changes to the MOSFLM package for processing film and image plate data" *Joint CCP4 + ESF-EAMCB Newsletter on Protein Crystallography* 26 (1992).

(56) References Cited

OTHER PUBLICATIONS

Liu, et al. "Optimization of Non-ATP Competitive CDK/Cyclin Groove Inhibitors through REPLACE-Mediated Fragment Assembly" *J. Med. Chem.* 56 (2013) pp. 1573-1582.
McInnes, C. "Ch. 12: REPLACE Strategy for generating Non-ATP competitive Inhibitors of Cell-Cycle Protein Kinases" *Protein-Protein Interactions in Drug Discovery* Wiley-VCH (2013) pp. 291-304.
McInnes, et al. "Targeting subcellular localization through the polo-box domain: non-ATP competitive inhibitors recapitulate a PLK1 phenotype" *Molec. Cancer Therapeutics* 11 (2012) pp. 1683-1692.
McInnes, C. "Progress in the development of Non-ATP competitive Protein Kinase Inhibitors for Oncology" *Annu. Rep. Med. Chem.* 47 (2012) pp. 459-474.
Michaloglou, et al. "$BRAF^{E600}$ in benign and malignant human tumours" *Oncogene* 27 (2008) pp. 877-895.
Misawa, et al. "Rapid and high-sensitivity cell-based assays of protein-protein interactions using split click beetle luciferase complementation: An approach to the study of G-protein-coupled receptors" *Anal. Chem.* 82 (2010) pp. 2552-2560.
Nielsen, et al. "Orally Absorbed Cyclic Peptides" *Chem. Rev.* 117 (2017) pp. 8094-8128.
Nieto, et al. "A Braf kinase-inactive mutant induces lung adenocarcinoma" *Nature* 548 (2017) pp. 239-243.
Otwinowski, et al. "Processing of x-ray diffraction data collected in oscillation mode" *Meth. Enzymol. A* 276 (1997) pp. 307-326.
Papaneophytou, et al. "Quantification of the effects of ionic strength, viscosity, and hydrophobicity on protein-ligand binding affinity" *ACS Med. Chem. Lett.* 5 (2014) pp. 931-936.
Pflugrath, J. "The finer things in X-ray diffraction data collection" *Acta Cryst.* D55 (1999) pp. 1718-1725.
Poulikakos, et al. "RAF inhibitor resistance is mediated by dimerization of aberrantly spliced $BRAF^{V600E}$" *Nature* 480 (2011) pp. 387-390.
Poulikakos, et al. "RAF inhibitors transactivate RAF dimers and ERK signalling in cells with wild-type BRAF" *Nature* 464 (2010) pp. 427-430.
Premnath, et al. "Iterative Conversion of Cyclin Binding Groove Peptides into Druglike CDK Inhibitors with Antitumor Activity" *J. Med. Chem.* 58 (2015) pp. 433-442.
Qin, et al. "Identification of a novel family of $BRAF^{V600E}$ inhibitors" *J. Med. Chem.* 55 (2012) pp. 5220-5230.
Rajakulendran, et al. "A dimerization-dependent mechanism drives RAF catalytic activation" *Nature* 461 (2009) pp. 542-545.
Röring, et al. "Distinct requirement for an intact dimer interface in wild-type, V600E and kinase-dead B-Raf signaling" *EMBO J.* 31 (2012) pp. 2629-2647.
Roskoski, Jr., R. "Classification of small molecule protein kinase inhibitors based upon the structures of their drug-enzyme complexes" *Pharmacol. Res.* 103 (2016) pp. 26-48.
Ross, et al. "The distribution of *BRAF* gene fusions in solid tumors and response to targeted therapy" *Int'l J. Cancer* 138 (2016) pp. 881-890.
Samatar, et al. "Targeting RAS-ERK signalling in cancer: promises and challenges" *Drug Discov.* 13 (2014) pp. 928-942.
Selt, et al. "Establishment and application of a novel patient-derived KIAA1549:BRAF-driven pediatric pilocytic astrocytoma model for preclinical drug testing" *Oncotarget* 8 (2017) pp. 11460-11479.
Shaw, et al. "Kinases and pseudokinases: Lessons from RAF" *Mol. Cell Biol.* 34 (2014) pp. 1538-1546.
Sherr, C.J. "Cancer cell cycles" *Science* 274 (1996) pp. 1672-1677.
Siegel, et al. "Cancer Statistics, 2020" *CA Cancer J. Clin.* 70 (2020) pp. 7-30.
Sievert, et al. "Paradoxical activation and RAF inhibitor resistance of BRAF protein kinase fusions characterizing pediatric astrocytomas" *PNAS* 110 (2013) pp. 5957-5962.
Sur, et al. "A panel of isogenic human cancer cells suggests a therapeutic approach for cancers with inactivated p53" *PNAS* 106(10) (2009) pp. 3964-3969.
Thevakumaran, et al. "Crystal structure of a BRAF kinase domain monomer explains basis for allosteric regulation" *Mol. Biol.* 22 (2015) pp. 37-43.
Thota, et al. "Trametinib in the treatment of melanoma" *Expert Opin. Biol. Ther.* 15 (2015) pp. 735-747.
Verdine, et al. "Stapled peptides for intracellular drug targets" *Meth. Enzymol.* 503 (2012) pp. 3-33.
Villar, et al. "How proteins bind macrocycles" *Chem. Biol.* 10 (2014) pp. 723-731.
Walensky, et al. "A stapled BID BH3 helix directly binds and activates BAX" *Mol. Cell.* 24 (2006) pp. 199-210.
Walensky, et al. "Activation of apoptosis in vivo by a hydrocarbon-stapled BH3 helix" *Science* 305 (2004) pp. 1466-1470.
Wargo, et al. "Universes Collide: Combining Immunotherapy with Targeted Therapy for Cancer" *Cancer Discov.* 4 (2014) pp. 1377-1386.
Weinberg, et al. "The Atypical Kinase RIOK1 Promotes Tumor Growth and Invasive Behavior" *EBioMedicine* 20 (2017) pp. 79-97.
Wimmer, et al. "Partner exchange: Protein-protein interactions in the Raf pathway" *Trends Biochem. Sci.* 35 (2010) pp. 660-668.
Wu, et al. "Increased BRAF heterodimerization is the common pathogenic mechanism for noonan syndrome-associated RAF1 mutants" *Mol. Cell. Biol.* 32 (2012) pp. 3872-3890.
Yaktapour, et al. "BRAF inhibitor-associated ERK activation drives development of chronic lymphocytic leukemia" *J. Clin. Invest.* 124 (2014) pp. 5074-5084.
Yang, et al. "DNA damage and homologous recombination signaling induced by thymidylate deprivation" *Biochem. Pharmacol.* 76 (2008) pp. 987-996.
Yao, et al. "Tumours with class 3 BRAF mutants are sensitive to the inhibition of activated RAS" *Nature* 548 (2017) pp. 234-238.
Yao, et al. "BRAF Mutants Evade ERK-Dependent Feedback by Different Mechanisms that Determine Their Sensitivity to Pharmacologic Inhibition" *Cancer Cell* 28 (2015) pp. 370-383.
Yuan, et al. "Development of siRNA payloads to target KRAS-mutant cancer" *Cancer Discov.* 4 (2014) pp. 1182-1197.

* cited by examiner

| ID | BRAF Residues | Sequence | Kd (μM) |
|---|---|---|---|
| 1 | 503-521 | GVLRKTRHVNILLFMGYST | 3.84 ±0.32 |
| 2 | 503-521 R509H, L515G, M517W | GVLRKTHHVNILGFWGYST | NB |
| 3 | scrambled | GRINKGRHTFLLVVMTYSL | 2.96 ± 0.18 |
| 4 | 503-521 L505A | GVARKTRHVNILLFMGYST | 3.89 ±0.53 |
| 5 | 503-521 R506E | GVLEKTRHVNILLFMGYST | 1.09 ±0.29 |
| 6 | 503-521 R506L | GVLLKTRHVNILLFMGYST | 0.54 ±0.11 |
| 7 | 503-521 T508D | GVLRKDRHVNILLFMGYST | 2.2 ±0.83 |
| 8 | 503-521 T508A | GVLRKARHVNILLFMGYST | 2.8 ±0.29 |
| 9 | 503-521 H510F | GVLRKTRFVNILLFMGYST | NB |
| 10 | 503-521 V511A | GVLRKTRHANILLFMGYST | 4.75 ±1.7 |
| 11 | 503-521 L514A | GVLRKTRHVNIALFMGYST | 9.8 ±1.6 |
| 12 | 503-521 L515I | GVLRKTRHVNILIFMGYST | 4.1 ±1.1 |
| 13 | 503-521 L515homoleucine | GVLRKTRHVNIL{HL}FMGYST | 1.25 ±0.36 |
| 14 | 503-521 F516D | GVLRKTRHVNILLDMGYST | NB |
| 15 | 503-518 | GVLRKTRHVNILLFMG | 1.88 ±0.36 |

FIG. 1

| SEQ ID NO: | BRAF Residues | Sequence | Kd (μM) |
|---|---|---|---|
| 16 | 504-517 | VLRKTRHVNILLFM | 5.75 ± 1.2 |
| 17 | 504-518 | VLRKTRHVNILLFMG | 0.13 ±0.040 |
| 18 | 504-518 | VLRKTRHVNILLFMG-$NH_2$ | 0.48 ±0.091 |
| 19 | 504-518 | Ac-VLRKTRHVNILLFMG | 0.8 ±0.083 |
| 20 | 504-518 L515homoleucine | VLRKARHVNIL(HL)FMG | 0.49 ±0.16 |
| 21 | 504-518 L505A | VARKTRHVNILLFMG | 0.45 ±0.03 |
| 22 | 504-518 R506A | VLAKTRHVNILLFMG | 0.36 ±0.03 |
| 23 | 504-518 K507A | VLRATRHVNILLFMG | NT |
| 24 | 504-518 R509A | VLRKTAHVNILLFMG | 2.4 ±0.35 |
| 25 | 504-518 H510A | VLRKTRAVNILLFMG | 2.7 ±0.4 |
| 26 | 504-518 N512A | VLRKTRHVAILLFMG | NB |
| 27 | 504-518 I513A | VLRKTRHVNALLFMG | 2.69± 0.35 |
| 28 | 504-518 L514A | VLRKTRHVNIALFMG | 1.02 ±0.14 |
| 29 | 504-518 F516A | VLRKTRHVNILLAMG | 0.57 ±0.08 |
| 30 | 504-518 M517A | VLRKTRHVNILLFAG | 0.54 ±0.15 |
| 31 | 505-518 | LRKTRHVNILLFMG | 0.19 ±0.13 |
| 32 | 505-518 R506L | LLKTRHVNILLFMG | 0.55 ±0.105 |

FIG. 8

| SEQ ID NO: | BRAF Residues | Sequence | Kd (μM) |
|---|---|---|---|
| 33 | cyclo 504-518 L505C, F516C | VCRKTRHVNILLCM | 0.36 ±0.32 |
| 34 | 508-513 T508O, N512A, I513E | LRKORHVAELLFMG | NB |
| 35 | cyclo 508-513 T508O, I513E | LRKORHVNELLFMG | 0.78 ±0.10 |
| 36 | cyclo 508-513 T508O, N512A, I513E | LRKORHVAELLFMG | 0.46 ±0.04 |
| 37 | cyclo 508-513 T508K, I513E | LRKKRHVNELLFMG | 1.89±0.33 |
| 38 | cyclo 508-513 T508K, N512A, I513E | LRKKRHVAELLFMG | 0.061±0.01 |

FIG. 9

| SEQ ID NO | Purity | Column Dimensions | Method |
|---|---|---|---|
| 1 | >90% | 4.6 x 250 mm | 5-65% acetonitrile/water/0.1%TFA/25 min |
| 2 | >90% | 4.6 x 250 mm | 5-65% acetonitrile/water/0.1%TFA/25 min |
| 3 | >90% | 4.6 x 250 mm | 5-65% acetonitrile/water/0.1%TFA/25 min |
| 4 | >90% | 4.6 x 250 mm | 5-65% acetonitrile/water/0.1%TFA/25 min |
| 5 | >90% | 4.6 x 250 mm | 5-65% acetonitrile/water/0.1%TFA/25 min |
| 6 | >90% | 4.6 x 250 mm | 5-65% acetonitrile/water/0.1%TFA/25 min |
| 7 | >90% | 4.6 x 250 mm | 5-65% acetonitrile/water/0.1%TFA/25 min |
| 8 | >90% | 4.6 x 250 mm | 5-65% acetonitrile/water/0.1%TFA/25 min |
| 9 | >90% | 4.6 x 250 mm | 5-65% acetonitrile/water/0.1%TFA/25 min |
| 10 | >90% | 4.6 x 250 mm | 5-65% acetonitrile/water/0.1%TFA/25 min |
| 11 | >90% | 4.6 x 250 mm | 5-65% acetonitrile/water/0.1%TFA/25 min |
| 12 | >90% | 4.6 x 250 mm | 5-65% acetonitrile/water/0.1%TFA/25 min |
| 13 | >90% | 4.6 x 250 mm | 5-65% acetonitrile/water/0.1%TFA/25 min |
| 14 | >90% | 4.6 x 250 mm | 5-65% acetonitrile/water/0.1%TFA/25 min |
| 15 | >90% | 4.6 x 250 mm | 5-65% acetonitrile/water/0.1%TFA/25 min |
| 16 | >90% | 4.6 x 250 mm | 5-65% acetonitrile/water/0.1%TFA/25 min |
| 17 | >90% | 4.6 x 250 mm | 5-65% acetonitrile/water/0.1%TFA/25 min |
| 18 | >90% | 4.6 x 250 mm | 5-65% acetonitrile/water/0.1%TFA/25 min |
| 19 | >90% | 4.6 x 250 mm | 5-65% acetonitrile/water/0.1%TFA/25 min |
| 20 | >90% | 4.6 x 250 mm | 5-65% acetonitrile/water/0.1%TFA/25 min |
| 21 | >90% | 4.6 x 250 mm | 5-65% acetonitrile/water/0.1%TFA/25 min |
| 22 | >90% | 4.6 x 250 mm | 5-95% acetonitrile/water/0.1%TFA/35 min |
| 23 | >90% | 4.6 x 250 mm | 5-65% acetonitrile/water/0.1%TFA/25 min |
| 24 | >90% | 4.6 x 250 mm | 5-65% acetonitrile/water/0.1%TFA/25 min |
| 25 | >90% | 4.6 x 250 mm | 5-65% acetonitrile/water/0.1%TFA/25 min |
| 26 | >90% | 4.6 x 250 mm | 5-65% acetonitrile/water/0.1%TFA/25 min |
| 27 | >90% | 4.6 x 250 mm | 5-65% acetonitrile/water/0.1%TFA/25 min |
| 28 | >90% | 4.6 x 250 mm | 5-65% acetonitrile/water/0.1%TFA/25 min |
| 29 | >90% | 4.6 x 250 mm | 5-65% acetonitrile/water/0.1%TFA/25 min |
| 30 | >90% | 4.6 x 250 mm | 5-65% acetonitrile/water/0.1%TFA/25 min |
| 31 | >90% | 4.6 x 250 mm | 5-65% acetonitrile/water/0.1%TFA/25 min |
| 32 | >90% | 4.6 x 250 mm | 5-95% acetonitrile/water/0.1%FA/30 min |
| 33 | >90% | 4.6 x 250 mm | 5-65% acetonitrile/water/0.1%TFA/25 min |
| 34 | 96% | 4.6 x 250 mm | 5-95% acetonitrile/water/0.1%FA/40 min |
| 35 | >95% | 4.6 x 250 mm | 5-95% acetonitrile/water/0.1%FA/30 min |
| 36 | 87% | 4.6 x 250 mm | 5-95% acetonitrile/water/0.1%FA/30 min |
| 37 | >90% | 4.6 x 250 mm | 5-95% acetonitrile/water/0.1%FA/30 min |
| 38 | >90% | 4.6 x 250 mm | 5-95% acetonitrile/water/0.1%FA/30 min |

FIG. 10A

| SEQ ID NO | FlowRate | Retention Time | Theoretical MW | Observed MW |
|---|---|---|---|---|
| 1 | 1ml/min | 20.3 | 2205.6 | 2205.0 |
| 2 | 1ml/min | 19.3 | 2185.5 | 2186.1 |
| 3 | 1ml/min | 20.7 | 2205.6 | 2205.9 |
| 4 | 1ml/min | 17.1 | 2163.5 | 2163.3 |
| 5 | 1ml/min | 19.9 | 2178.6 | 2178.2 |
| 6 | 1ml/min | 19.4 | 2162.6 | 2162.4 |
| 7 | 1ml/min | 18.2 | 2219.6 | 2219.4 |
| 8 | 1ml/min | 17.7 | 2175.6 | 2175.3 |
| 9 | 1ml/min | 20.2 | 2215.7 | 2215.3 |
| 10 | 1ml/min | 18.3 | 2177.6 | 2177.2 |
| 11 | 1ml/min | 17.0 | 2163.6 | 2163.4 |
| 12 | 1ml/min | 18.6 | 2205.6 | 2205.4 |
| 13 | 1ml/min | 20.1 | 2219.6 | 2219.4 |
| 14 | 1ml/min | 17.7 | 2173.6 | 2173.3 |
| 15 | 1ml/min | 17.7 | 1854.3 | 1853.9 |
| 16 | 1ml/min | 17.7 | 1740.2 | 1739.9 |
| 17 | 1ml/min | 17.0 | 1797.2 | 1797.5 |
| 18 | 1ml/min | 18.9 | 1796.2 | 1796.1 |
| 19 | 1ml/min | 14.8 | 1839.3 | 1839.7 |
| 20 | 1ml/min | 13.1 | 1781.2 | 1781.2 |
| 21 | 1ml/min | 15.0 | 1755.2 | 1755.2 |
| 22 | 1ml/min | 15.5 | 1712.1 | 1712.4 |
| 23 | 1ml/min | 15.9 | 1740.1 | 1740.2 |
| 24 | 1ml/min | 19.4 | 1712.1 | 1712.0 |
| 25 | 1ml/min | 13.6 | 1731.2 | 1731.5 |
| 26 | 1ml/min | 17.5 | 1754.2 | 1754.2 |
| 27 | 1ml/min | 17.8 | 1755.2 | 1755.3 |
| 28 | 1ml/min | 16.4 | 1755.2 | 1755.5 |
| 29 | 1ml/min | 13.9 | 1721.1 | 1721.3 |
| 30 | 1ml/min | 15.3 | 1737.1 | 1737.2 |
| 31 | 1ml/min | 18.8 | 1698.1 | 1697.5 |
| 32 | 1ml/min | 16.7 | 1655.1 | 1655.0 |
| 33 | 1ml/min | 17.5 | 1684.1 | 1683.5 |
| 34 | 1ml/min | 17.6 | 1683.1 | 1682.0 |
| 35 | 1ml/min | 17.2 | 1707.0 | 1708.0 |
| 36 | 1ml/min | 17.4 | 1664.0 | 1664.0 |
| 37 | 1ml/min | 17.7 | 1722.1 | 1724.0 |
| 38 | 1ml/min | 18.2 | 1679.1 | 1680.0 |

FIG. 10B

Peptide I

Peptide II

Peptide III

5-FAM-
Peptide II

5-FAM-
Peptide III

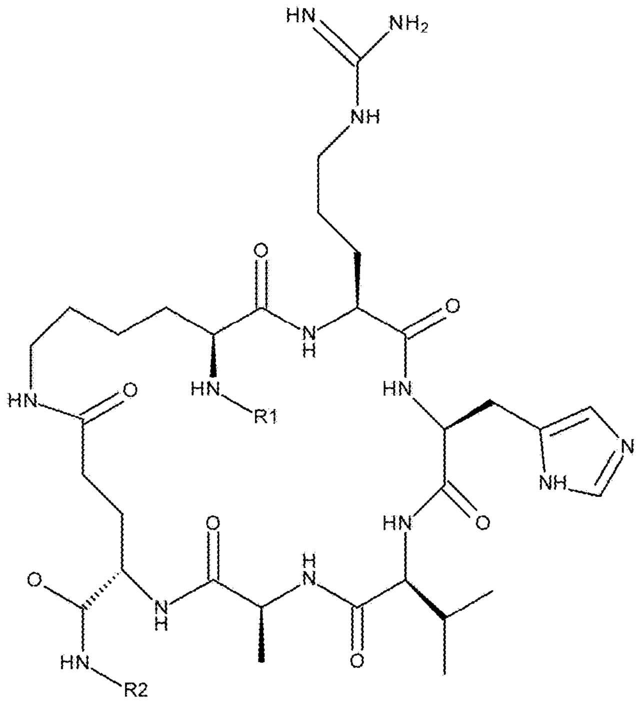
| R1 | N Cap structure | R2 | CAS# of precursor | Interaction Energy | NCap IE Total incl. lysine | Cap group contribution only |
|---|---|---|---|---|---|---|
| - | Lys | LLFMG-NH2 | N/A | -80.2 | -9.0 | - |
| N1 | 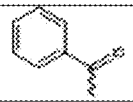 | LLFMG-NH2 | 65-85-0 | -87.6 | -15.9 | -6.9 |
| N2 | 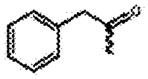 | LLFMG-NH2 | 103-82+2 | -89.6 | -16.4 | -7.4 |
| N3 | 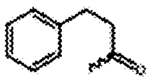 | LLFMG-NH2 | 501-52-0 | -85.7 | -13.0 | -4.0 |
| N4 | 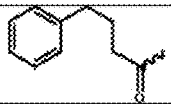 | LLFMG-NH2 | 1821-12-1 | -86.8 | -14.0 | -5.0 |
FIG. 12

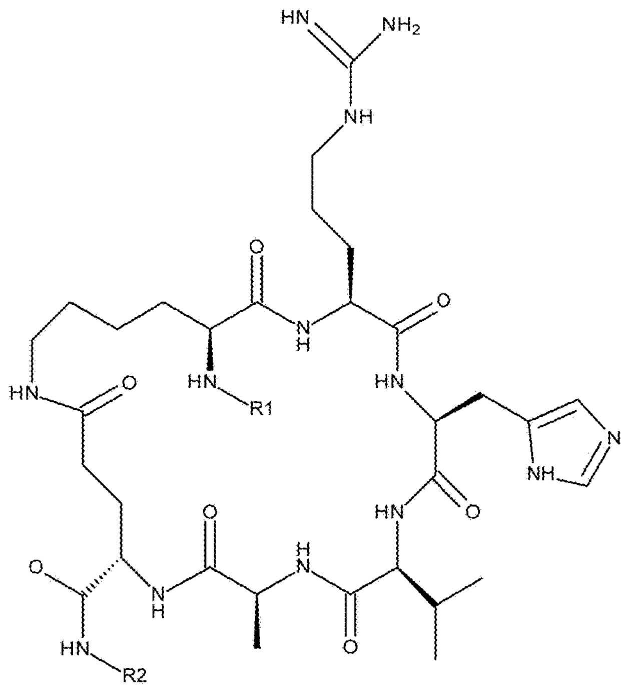
| R1 | R2 | C-Cap Structure | Chembridge ID | Interaction Energy | Capping Group IE |
|---|---|---|---|---|---|
| Ac-LRK | | Leu-Leu | N/A | -80.2 | -5.29 |
| Ac-LRK | C1 | 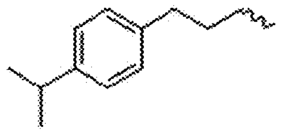 | 4016878 | -77.8 | -6.83 |
| Ac-LRK | C2 | 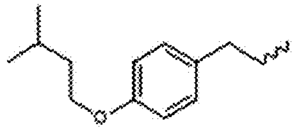 | 403222 | -90 | -14.64 |
| Ac-LRK | C3 | 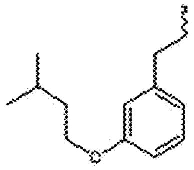 | 4033933 | -90.5 | -16.22 |
| Ac-LRK | C4 | 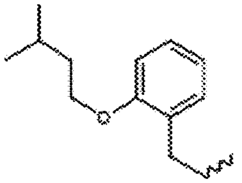 | 4033656 | -80.99 | -4.81 |
FIG. 13

| SEQ ID NO: | N-Cap | C-Cap | Kd (ITF) (μM) |
|---|---|---|---|
| 17 (VLRKTRHVNILLFMG) | - | - | 1.88 ± 0.036 |
| 48 (KRHVAE) | - | - | 0.30 ± 0.03 |
| 45 (TRHVNILLFMG) | N1 | - | 0.05 ± 0.006 |
| 45 | N2 | - | 0.084 ± 0.024 |
| 45 | N3 | - | - |
| 45 | N4 | - | - |
| 46 (LKRTRHVNI) | - | C2 | 0.02 ± 0.010 |
| 46 | - | C3 | 0.380 ± 0.096 |
| 46 | - | C4 | 0.570 ± 0.092 |
| 62 (KRHVNE) | N1 | C2 | - |
| 63 (TRHVNI) | N2 | C4 | 0.280 ± 0.088 |
| 64 (KMeRaPAE) | N1 | C2 | 0.017 ± 0.006 |
N1
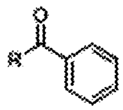
N2
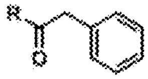
N3
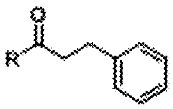
N4
C2
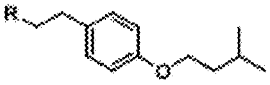
C3
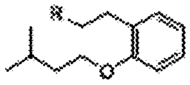
C4
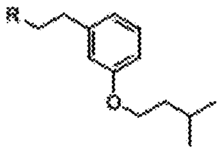
FIG. 14

| SEQ ID NO | BRAF residues, modification | Sequence |
|---|---|---|
| 50 | 504-519, L505K, G518E | VKRKTRHVNILLFMEY |
| 51 | 504-519, L505O, G518E | VORKTRHVNILLFMEY |
| 52 | 504-518, T508O | VLRKORHVNELLFMG |
| 53 | 504-518, T508K | VLRKKRHVNELLFMG |
| 54 | 504-518, L505Dab, T508K, I513E, F516D | VDabRKKRHVNELLDMG |
| 55 | 504-518, T508O, N512A, I513E | VLRKORHVAELLFMG |
| 56 | 505-518, T508O, N512A, I513E | LRKORHVAELLFMG |
| 57 | 504-518, T508O, N512A, I513E, L515hL | VLRKORHVAELhLFMG |
| 58 | 504-518, T508O, N512A, I513E, L515I | VLRKORHVAELIFMG |
| 59 | 504-518, T508K, N512A, I513E | VLRKKRHVAELLFMG |
| 60 | 504-518, T508K, R509MeR, N512A, I513E | VLRKKMeRHVAELLFMG |
| 61 | 507-518, T508K, V511P, N512A, I513E | KRHPAELLFMG |
| 62 | 508-513, T508K, I513E | KRHVNE |

FIG. 15

SEQUENCE LISTING

```
<160> NUMBER OF SEQ ID NOS: 69

<210> SEQ ID NO 1
<211> LENGTH: 19
<212> TYPE: PRT
<213> ORGANISM: Homo sapiens

<400> SEQUENCE: 1

Gly Val Leu Arg Lys Thr Arg His Val Asn Ile Leu Leu Phe Met Gly
1               5                   10                  15
```

-continued

Tyr Ser Thr

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

```
Gly Val Leu Arg Lys Thr His His Val Asn Ile Leu Gly Phe Trp Gly
1               5                   10                  15

Tyr Ser Thr
```

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

```
Gly Arg Ile Asn Lys Gly Arg His Thr Phe Leu Leu Val Val Met Thr
1               5                   10                  15

Tyr Ser Leu
```

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

```
Gly Val Ala Arg Lys Thr Arg His Val Asn Ile Leu Leu Phe Met Gly
1               5                   10                  15

Tyr Ser Thr
```

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

```
Gly Val Leu Glu Lys Thr Arg His Val Asn Ile Leu Leu Phe Met Gly
1               5                   10                  15

Tyr Ser Thr
```

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

```
Gly Val Leu Leu Lys Thr Arg His Val Asn Ile Leu Leu Phe Met Gly
1               5                   10                  15
```

-continued

Tyr Ser Thr

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

```
Gly Val Leu Arg Lys Asp Arg His Val Asn Ile Leu Leu Phe Met Gly
1               5                   10                  15

Tyr Ser Thr
```

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

```
Gly Val Leu Arg Lys Ala Arg His Val Asn Ile Leu Leu Phe Met Gly
1               5                   10                  15

Tyr Ser Thr
```

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

```
Gly Val Leu Arg Lys Thr Arg Phe Val Asn Ile Leu Leu Phe Met Gly
1               5                   10                  15

Tyr Ser Thr
```

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Gly Val Leu Arg Lys Thr Arg His Ala Asn Ile Leu Leu Phe Met Gly
1               5                   10                  15

Tyr Ser Thr
```

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
Gly Val Leu Arg Lys Thr Arg His Val Asn Ile Ala Leu Phe Met Gly
```

-continued 1 5 10 15

Tyr Ser Thr

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gly Val Leu Arg Lys Thr Arg His Val Asn Ile Leu Ile Phe Met Gly
1 5 10 15

Tyr Ser Thr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (13)..(13)
<223> OTHER INFORMATION: Homoleucine

<400> SEQUENCE: 13

Gly Val Leu Arg Lys Thr Arg His Val Asn Ile Leu Leu Phe Met Gly
1 5 10 15

Tyr Ser Thr

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Gly Val Leu Arg Lys Thr Arg His Val Asn Ile Leu Leu Asp Met Gly
1 5 10 15

Tyr Ser Thr

<210> SEQ ID NO 15
<211> LENGTH: 16
<212> TYPE: PRT
<213> ORGANISM: Homo sapiens

<400> SEQUENCE: 15

Gly Val Leu Arg Lys Thr Arg His Val Asn Ile Leu Leu Phe Met Gly
1 5 10 15

<210> SEQ ID NO 16
<211> LENGTH: 14
<212> TYPE: PRT
<213> ORGANISM: Homo sapiens

<400> SEQUENCE: 16

Val Leu Arg Lys Thr Arg His Val Asn Ile Leu Leu Phe Met
1 5 10

<210> SEQ ID NO 17
<211> LENGTH: 15
<212> TYPE: PRT
<213> ORGANISM: Homo sapiens

<400> SEQUENCE: 17

Val Leu Arg Lys Thr Arg His Val Asn Ile Leu Leu Phe Met Gly
1 5 10 15

<210> SEQ ID NO 18
<211> LENGTH: 15
<212> TYPE: PRT
<213> ORGANISM: Homo sapiens

<400> SEQUENCE: 18

Val Leu Arg Lys Thr Arg His Val Asn Ile Leu Leu Phe Met Gly
1 5 10 15

<210> SEQ ID NO 19
<211> LENGTH: 15
<212> TYPE: PRT
<213> ORGANISM: Homo sapiens

<400> SEQUENCE: 19

Val Leu Arg Lys Thr Arg His Val Asn Ile Leu Leu Phe Met Gly
1 5 10 15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (12)..(12)
<223> OTHER INFORMATION: Homoleucine

<400> SEQUENCE: 20

Val Leu Arg Lys Ala Arg His Val Asn Ile Leu Leu Phe Met Gly
1 5 10 15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Val Ala Arg Lys Thr Arg His Val Asn Ile Leu Leu Phe Met Gly
1 5 10 15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Val Leu Ala Lys Thr Arg His Val Asn Ile Leu Leu Phe Met Gly
1 5 10 15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Val Leu Arg Ala Thr Arg His Val Asn Ile Leu Leu Phe Met Gly
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Val Leu Arg Lys Thr Ala His Val Asn Ile Leu Leu Phe Met Gly
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Val Leu Arg Lys Thr Arg Ala Val Asn Ile Leu Leu Phe Met Gly
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Val Leu Arg Lys Thr Arg His Val Ala Ile Leu Leu Phe Met Gly
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Val Leu Arg Lys Thr Arg His Val Asn Ala Leu Leu Phe Met Gly
1 5 10 15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

-continued

```
Val Leu Arg Lys Thr Arg His Val Asn Ile Ala Leu Phe Met Gly
1               5                   10                  15


<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Leu Arg Lys Thr Arg His Val Asn Ile Leu Leu Ala Met Gly
1               5                   10                  15


<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Leu Arg Lys Thr Arg His Val Asn Ile Leu Leu Phe Ala Gly
1               5                   10                  15


<210> SEQ ID NO 31
<211> LENGTH: 14
<212> TYPE: PRT
<213> ORGANISM: Homo sapiens

<400> SEQUENCE: 31

Leu Arg Lys Thr Arg His Val Asn Ile Leu Leu Phe Met Gly
1               5                   10


<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Leu Lys Thr Arg His Val Asn Ile Leu Leu Phe Met Gly
1               5                   10


<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Cys Arg Lys Thr Arg His Val Asn Ile Leu Leu Cys Met
1               5                   10


<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

-continued

<220> FEATURE:
<221> NAME/KEY: MOD_RES
<222> LOCATION: (4)..(4)
<223> OTHER INFORMATION: Ornithine

<400> SEQUENCE: 34

Leu Arg Lys Xaa Arg His Val Ala Glu Leu Leu Phe Met Gly
1 5 10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Ornithine

<400> SEQUENCE: 35

Leu Arg Lys Xaa Arg His Val Asn Glu Leu Leu Phe Met Gly
1 5 10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Ornithine

<400> SEQUENCE: 36

Leu Arg Lys Xaa Arg His Val Ala Glu Leu Leu Phe Met Gly
1 5 10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Leu Arg Lys Lys Arg His Val Asn Glu Leu Leu Phe Met Gly
1 5 10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Leu Arg Lys Lys Arg His Val Ala Glu Leu Leu Phe Met Gly
1 5 10

<210> SEQ ID NO 39
<211> LENGTH: 20
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 39

Ala Gly Val Leu Glu Lys Thr Arg His Val Asn Ile Leu Leu Phe Met
1               5                   10                  15

Gly Tyr Ser Thr
            20


<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ala Val Leu Glu Lys Thr Arg His Val Asn Ile Leu Leu Phe Met
1               5                   10                  15

Gly Tyr Ser Thr
            20


<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Val Leu Glu Lys Thr Arg His Val Asn Ile Leu Leu Phe Met Gly
1               5                   10                  15

Tyr Ser Thr Ala
            20


<210> SEQ ID NO 42
<211> LENGTH: 12
<212> TYPE: PRT
<213> ORGANISM: Homo sapiens

<400> SEQUENCE: 42

Lys Thr Arg His Val Asn Ile Leu Leu Phe Met Gly
1               5                   10


<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Arg His Val Asn Leu Leu Phe Met Gly
1               5                   10


<210> SEQ ID NO 44
<211> LENGTH: 5
<212> TYPE: PRT
<213> ORGANISM: Homo sapiens

<400> SEQUENCE: 44
```

Leu Leu Phe Met Gly
1 5

<210> SEQ ID NO 45
<211> LENGTH: 11
<212> TYPE: PRT
<213> ORGANISM: Homo sapiens

<400> SEQUENCE: 45

Thr Arg His Val Asn Ile Leu Leu Phe Met Gly
1 5 10

<210> SEQ ID NO 46
<211> LENGTH: 9
<212> TYPE: PRT
<213> ORGANISM: Homo sapiens

<400> SEQUENCE: 46

Leu Lys Arg Thr Arg His Val Asn Ile
1 5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Lys Arg His Val Ala Glu Leu Leu Phe Met Gly
1 5 10

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Lys Arg His Val Ala Glu
1 5

<210> SEQ ID NO 49
<211> LENGTH: 3
<212> TYPE: PRT
<213> ORGANISM: Homo sapiens

<400> SEQUENCE: 49

Leu Arg Lys
1

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Val Lys Arg Lys Thr Arg His Val Asn Ile Leu Leu Phe Met Glu Tyr
1 5 10 15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Ornithine

<400> SEQUENCE: 51

Val Xaa Arg Lys Thr Arg His Val Asn Ile Leu Leu Phe Met Glu Tyr
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Ornithine

<400> SEQUENCE: 52

Val Leu Arg Lys Xaa Arg His Val Asn Glu Leu Leu Phe Met Gly
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Val Leu Arg Lys Lys Arg His Val Asn Glu Leu Leu Phe Met Gly
1 5 10 15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: D-aminobutanoic acid

<400> SEQUENCE: 54

Val Xaa Arg Lys Lys Arg His Val Asn Glu Leu Leu Asp Met Gly
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Ornithine

<400> SEQUENCE: 55

Val Leu Arg Lys Xaa Arg His Val Ala Glu Leu Leu Phe Met Gly
1 5 10 15

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Ornithine

<400> SEQUENCE: 56

Leu Arg Lys Xaa Arg His Val Ala Glu Leu Leu Phe Met Gly
1 5 10

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Ornithine
<220> FEATURE:
<221> NAME/KEY: MOD_RES
<222> LOCATION: (12)..(12)
<223> OTHER INFORMATION: Homoleucine

<400> SEQUENCE: 57

Val Leu Arg Lys Xaa Arg His Val Ala Glu Leu Leu Phe Met Gly
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Ornithine

<400> SEQUENCE: 58

Val Leu Arg Lys Xaa Arg His Val Ala Glu Leu Ile Phe Met Gly
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Val Leu Arg Lys Lys Arg His Val Ala Glu Leu Leu Phe Met Gly
1 5 10 15

```
<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N-methylated arginine

<400> SEQUENCE: 60

Val Leu Arg Lys Lys Arg His Val Ala Glu Leu Leu Phe Met Gly
1               5                   10                  15


<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Arg His Pro Ala Glu Leu Leu Phe Met Gly
1               5                   10


<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Arg His Val Asn Glu
1               5


<210> SEQ ID NO 63
<211> LENGTH: 6
<212> TYPE: PRT
<213> ORGANISM: Homo sapiens

<400> SEQUENCE: 63

Thr Arg His Val Asn Ile
1               5


<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methylated arginine
<220> FEATURE:
<221> NAME/KEY: MOD_RES
<222> LOCATION: (3)..(3)
<223> OTHER INFORMATION: D-alanine

<400> SEQUENCE: 64

Lys Arg Ala Pro Ala Glu
1               5
```

<210> SEQ ID NO 65
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N-methylated arginine

<400> SEQUENCE: 65

Lys Arg
1

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Lys Arg His Val Ala Glu Leu Leu Phe Met Gly
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Arg Lys Lys Arg His Val Ala Glu
1               5

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Val Leu Ala Ala Thr Ala Ala Val Asn Ala Leu Leu Phe Ala Gly
1               5                   10                  15

Tyr Ser Thr

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Arg Lys Lys Arg Arg Gln Arg Arg Arg
1               5                   10

OPTIMIZATION OF TYPE IV BRAF INHIBITORS FOR THE TREATMENT OF MELANOMA

CROSS REFERENCE TO RELATED APPLICATION

This application claims filing benefit of U.S. Provisional Application Ser. No. 63/104,268, having a filing date of Oct. 22, 2020, entitled "Design and Optimization of Type IV BRAF inhibitors for the Treatment of Metastatic Melanoma," which is incorporated herein by reference in its entirety.

FEDERAL RESEARCH STATEMENT

This invention was made with Government support under Grant No. R21 CA191899, awarded by National Institutes of Health. The Government has certain rights in the invention.

SEQUENCE LISTING

This application contains a Sequence Listing which has been submitted electronically in ASCII format and is hereby incorporated by reference in its entirety. Said ASCII copy, created on Oct. 27, 2021, is named USC-680 Sequence List.txt and is 319,048 bytes in size.

BACKGROUND

Tumors with mutant RAF kinases and mutant RAS enzymes represent some of the deadliest forms of cancer, including metastatic melanomas and pancreatic cancers. These two protein families are involved in the transduction of extracellular growth signals to the nucleus to regulate cell proliferation and differentiation, and both proteins are often involved in a pathway affected in tumor formation. Considerable efforts in drug discovery have been invested in modifying the signal transduction pathways associated with RAF kinases (A-Raf, B-Raf, and Raf-1/ C), yet there is still a need for further efforts as drug resistance and heterogeneity of tumor cells can pose challenges to single drug treatments.

Oncogenic RAS signaling occurs in about 30% of all human cancers and triggers homo- or hetero-dimerization of RAF kinases that is critical for several aspects of signal propagation through downstream MEK and ERK kinases. Despite intense efforts, pharmacologic inhibition of RAS proteins themselves and inhibition of their downstream effector kinases has so far been unsuccessful in treating RAS-driven tumors. Indeed, ATP-competitive RAF inhibitors cause the so-called paradoxical ERK activation in this context, and therefore, should not be used to treat RAS mutant tumors. This phenomenon is caused by drug-bound B-Raf molecules that promote activation of drug-free RAF protomers in the context of excessive RAS signaling via an allosteric mechanism.

There is a huge unmet medical need for improved treatment options for patients worldwide. For instance, while drugs that inhibit B-Raf, called paradox breakers, have been developed, such drugs have proven ineffective in tumors that have acquired mutant forms of the kinase. What are needed in the art are materials that can exhibit effectiveness against RAF kinases, and are particularly against mutant forms of these proteins.

SUMMARY

Embodiments of the disclosure are directed to peptides that display a binding affinity for the dimer interface of a Raf kinase protein, methods for modifying RAF kinase dimerization, and methods for inhibiting tumor growth. An embodiment of the disclosure is a peptide generated by modifying SEQ ID NO: 1. SEQ ID NO: 1 corresponds to amino acids 503-521 of B-Raf kinase and the peptide displays a binding affinity ($K_d$) of about 3.84 μM for the dimer interface of B-Raf.

In one embodiment, a peptide can include no more than 19 amino acid residues, can include a macrocycle that includes 5 or more amino acid residues in the ring structure, and can include one or more modifications that include substitution of one or more amino acid residues of SEQ ID NO: 1.

In one embodiment, a peptide can include one or more modifications to SEQ ID NO: 1, can include no more than 19 amino acid residues, and can include a non-peptidic N-terminal capping group and/or a non-peptidic C-terminal capping group.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 1 illustrates a table providing the SEQ ID NOs (ID=SEQ ID NO in Table) of exemplary peptides. The table includes a description of modifications made to the starting B-Raf peptide (SEQ ID NO:1) along with the resulting peptide sequences. A measured dissociation constant $K_d$ is also provided for each peptide.

FIG. 8 illustrates a table providing the SEQ ID NOs of exemplary peptides. The table includes a description of modifications made to the starting B-Raf peptide (SEQ ID NO: 1) along with the resulting peptide sequences. A measured dissociation constant $K_d$ is provided for each peptide.

FIG. 9 illustrates a table providing the SEQ ID NOs of exemplary peptides. The table includes a description of modifications made to the starting B-Raf peptide (SEQ ID NO: 1) along with the resulting peptide sequences. A measured dissociation constant $K_d$ is provided for each peptide.

FIG. 10A provides a table displaying the conditions used in an LCMS analysis of SEQ ID NOs 1-38, including column dimensions and method.

FIG. 10B illustrates a table displaying the conditions used in the LCMS analysis, including the flow rate, retention time, theoretical molecular weight, and observed molecular weight for SEQ ID NOs 1-38.

FIG. 12 illustrates a chemical structure for cyclic peptide inhibitors developed using the REPLACE strategy in accordance with example embodiments of the disclosure. The cyclic peptides are based upon KRHVAELLFMG (SEQ ID NO: 47) and include KRHVAE (SEQ ID NO: 48) in the cyclic portion and LLFMG (SEQ ID NO: 44) in a linear portion with various different N-capping groups.

FIG. 13 illustrates a chemical structure for cyclic peptide inhibitors developed using the REPLACE strategy in accordance with example embodiments of the disclosure. The cyclic peptides are based upon KRHVAE (SEQ ID NO: 48) in the cyclic portion and include an acetylated LRK (SEQ ID NO: 49) as an N-capping group and various C-capping groups.

FIG. 14 illustrates chemical structures of two peptide inhibitors developed using the REPLACE strategy in accordance with example embodiments of the disclosure. The peptides include SEQ ID NO: 45 and SEQ ID NO: 46 with an N-capping group and a C-capping group, as shown.

FIG. 15 illustrates a table providing the SEQ ID NOs of exemplary peptides. The table includes a description of modifications made to the starting B-Raf peptide (SEQ ID NO: 1) along with the resulting peptide sequences.

Figures 2A, 2B:
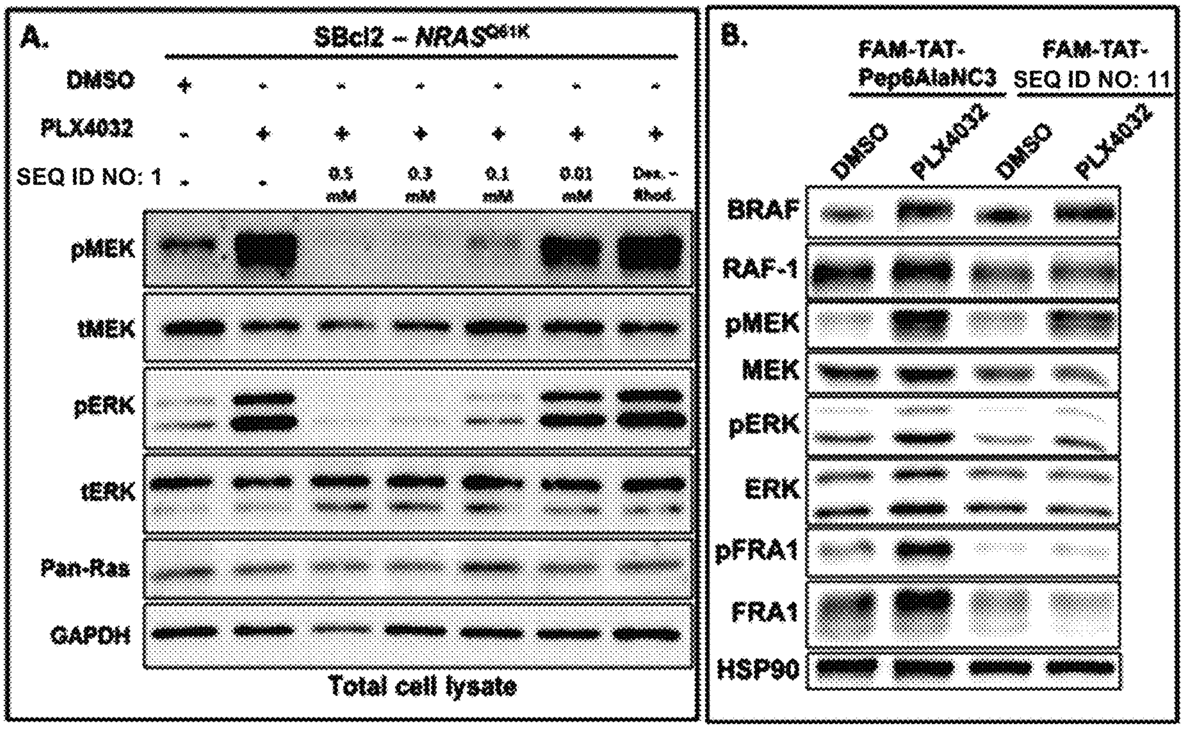
FIG. 2A illustrates a Western blot gel. The top portion shows the different conditions (DMSO, PLX4032, and Peptide 1) and the gel portion shows the stain for different antibodies specific to the proteins on the left (e.g., pMEK, tMEK, pERK, tERK, Pan-Ras, and GAPDH).
FIG. 2B illustrates a Western blot gel. The top portion shows the different conditions (DMSO and PLX4032 in conjunction with either FAM-TAT-Pep6AlaNC3 or FAM-TAT-Pep17) and the gel portion shows the stain for different antibodies specific to the proteins on the left (e.g., BRAF, RAF-1, pMEK, MEK, pERK, ERK, pFRA1, FRA1, HSP90).

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment may be used in another embodiment to yield a still further embodiment.

In general, disclosed herein are peptides that display a binding affinity for the dimer interface of a RAF kinase protein, methods for forming the peptides, and methods for using the peptides. By modifying dimerization, RAF kinase activity can be inhibited or reduced, for instance by allosteric binding.

An embodiment of the disclosure is a peptide that includes a modification to SEQ ID NO: 1. The peptide displays a binding affinity for at least part of the dimer interface of a RAF kinase protein. SEQ ID NO: 1 includes B-Raf residues 503-521 and has the following amino acid sequence:

SEQ ID NO: 1

GVLRKTRHVNILLFMGYST

A peptide as disclosed herein can include a sequence of amino acids that is based upon the reference sequence (e.g., SEQ ID NO: 1). The residues of a peptide can include residues substantially in the order of the same residues present in SEQ ID NO: 1, and in general, a peptide sequence does not include a scrambled or reordered form of the reference sequence. Further, a disclosed peptide can include a core sequence of 2 or more adjacent amino acids selected from the reference sequence. For embodiments of the disclosure, a modification can be applied to alter a sequence of the reference sequence, e.g., substitutions, functionalizations, etc.

The disclosed peptides can include at least 5 amino acids and can be developed from SEQ ID NO: 1. In some embodiments, a peptide can include at least two of R509, H510, or V511 of SEQ ID NO: 1. In an embodiment, a peptide can include R509 and the H510 of SEQ ID NO:1, can include H510 and the V511 of SEQ ID NO: 1, or can include all through of residues R509 to V511 from SEQ ID NO: 1 (i.e., RHV). In other embodiments, a peptide can include V511 to T515 of SEQ ID NO: 1, residues G503 to H510 of SEQ ID NO: 1, residues G513 to L514 of SEQ ID NO: 1, residues G501 to G518 of SEQ ID NO: 1, or residues T508 to I513 of SEQ ID NO: 1.

In some embodiments, a peptide can include 3, 4, 5, or more unmodified amino acids from the beginning, end, or a middle length of SEQ ID NO: 1 (e.g., SEQ ID NOs: 4-15). In certain embodiments, a peptide can include multiple amino acids from a middle segment of SEQ ID NO: 1 (e.g., SEQ ID NOs: 16-32), and one or more modifications can be made within the ordered sequence (e.g., SEQ ID NO: 22 shows B-Raf residues 504-518 including a modification at R506A). In some embodiments, a peptide can be truncated such that one or more terminal amino acids of SEQ ID NO: 1 have been deleted (e.g., SEQ ID NOs: 16-38, SEQ ID NOs: 42-65), optionally in conjunction with a modification to one or more residues remaining in the sequence. In some embodiments, the only residue modification to SEQ ID NO: 1 can be truncation of the sequence, e.g., SEQ ID NO: 15, SEQ ID NO: 16, SEQ ID NO: 17, SEQ ID NO: 31, SEQ ID NO: 42, SEQ ID NO: 45, SEQ ID NO: 46, SEQ ID NO: 63. In some embodiments, a peptide including an unmodified (or modified) sequence as compared to SEQ ID NO: 1 can be capped to form a BRAF inhibitor, as discussed further herein.

Certain embodiments of the disclosure include a peptide having an ordered sequence of more than 5 amino acids corresponding to a portion of SEQ ID NO: 1. In these embodiments, the composition can include a peptide that has at least 2, 3, 4, 5, 6, 7, 8, 9, 10, 12, 14, 16, 18 or 19 amino acids in an ordered sequence corresponding to SEQ ID NO: 1.

In embodiments of the disclosure, a peptide can include a modification to a portion of SEQ ID NO: 1. Modifications can encompass additions, deletions and/or substitutions to the amino acid residues of SEQ ID NO: 1. As an example, a peptide can include an ordered sequence corresponding to B-Raf residues 507-518 and include internal modification to that ordered sequence of SEQ ID NO: 1, e.g., a portion of SEQ ID NO: 1 such as KTRHVNILLFMG (SEQ ID NO: 42) can be further modified to include deletion of K507 and substitution of T508K to provide KRHVNLLFMG (SEQ ID NO: 43). As another example, the peptide can include an ordered sequence corresponding to B-Raf residues 504-518 of SEQ ID NO: 1 and including the substitution R506A (SEQ ID NO: 22).

In such embodiments, the modification can include an amino acid substitution where at least one of the amino acids of a portion of SEQ ID NO: 1 is substituted for a different amino acid. As an example, a peptide can be based upon residues 503-521 of SEQ ID NO: 1, and the peptide can include a substitution of arginine at the 506 position for glutamic acid (i.e., R506E). Thus, the peptide can have the sequence:

```
                                        (SEQ ID NO: 5)
                  GVLEKTRHVNILLFMGYST.
```

Modifications can also include an amino acid insertion. For example, a peptide based upon SEQ ID NO: 1 can include an alanine insertion before the 503 position, between the 503 and 504 position, or after the 521 position to produce, respectively: AGVLEKTRHVNILLFMGYST (SEQ ID NO: 39), GAVLEKTRHVNILLFMGYST (SEQ ID NO: 40), and GVLEKTRHVNILLFMGYSTA (SEQ ID NO: 41). Alanine substitutions can be carried out at any of several locations of SEQ ID NO: 1 to provide a peptide. For instance, alanine substitution can be carried out any of positions L505 through M517, optionally in conjunction with truncation of one or both ends of SEQ ID NO: 1, to form a peptide as described (see, e.g., SEQ ID NO: 21-30).

There are many natural amino acids, which occur as L-isomers in most living organisms; however, embodiments of the disclosure are not limited to only L-amino acids and can include modifications that substitute D-amino acids or other non-proteinogenic amino acids that are not naturally encoded by humans or any other organism. Herein, unless specifically referenced as a D-amino acid (i.e., the amino acid identifier followed by (d)), reference to a generic amino acid indicates the L-amino acid.

In embodiments of the disclosure, the peptide can include an ornithine (O) substitution to one or more residues of SEQ ID NO: 1. In some embodiments, a peptide may only include one or more amino acid substitutions of a human proteinogenic amino acids selected from the following group: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In still other embodiments, the modification can include a combination of a non-proteinogenic amino acid substitution and a human proteinogenic amino acid substitution. For instance, in some embodiments, a peptide can include a substitution of one or more residues of SEQ ID NO:1 for a D-aminobutanoic acid (Dab).

In an embodiment of the disclosure, the peptide having a modification can include substituting 2 or more amino acids of SEQ ID NO: 1 for alternative amino acids, optionally in conjunction with truncation of one or more amino acids from either or both ends of SEQ ID NO: 1. As an example, the 2 or more amino acid substitutions can include at least the substitutions: alanine for asparagine N512A and glutamic acid for isoleucine I513E as evidenced in SEQ ID NOs: 34, 36, 38, and 48 as well as in SEQ ID NOs: 55-61. As another example, the 2 or more amino acid substitutions can include substitution of a cysteine, lysine, or ornithine for leucine, e.g., L505C, L505K, L505Dab, or L505O and/or cysteine or aspartic acid for phenylalanine F516C, or F516D, and/or glutamic acid for glycine G518E as evidenced in SEQ ID NO: 33, 50, 51, and 54.

In some embodiments, a peptide can include a modification to a portion of SEQ ID NO: 1 that can include one or more of the following amino acid substitutions: L505A, L505C, L505K, L505O, L505Dab, R506E, R506L, T508D, T508A, T508O, T508K, H510F, H510H(d), H510V, H510L, V511A, V511P, N512A, I513E, L514A, L515I, L515homoleucine, F515D, F516C, F516D, M517S, M517T, M517N and G518E. In particular, this list of modifications is not meant to constrain the embodiments described herein. As noted above, alternative substitutions may be practiced without departing from the spirit and scope of this disclosure.

In any of the embodiments, the peptide can include structurally similar peptides to those disclosed herein. Structurally similar peptides can encompass variations such as the substitution of one amino acid having a first amino acid side chain with a second amino acid having a second amino acid side chain. Both the first amino acid side chain and the second amino acid side chain provide a similar characteristic to maintain structural similarity. A similar characteristic can include a side chain that has a similar polarity, charge, or size as the first amino acid side chain. As an example, leucine includes a hydrophobic side chain, which could be substituted with an isoleucine, valine, or alanine because each of these amino acids includes a hydrophobic side chain. As another example, histidine includes an aromatic side chain that can also carry a positive charge, which could be substituted with either amino acids that include aromatic side chain or with amino acids that can carry a positive charge such as, phenylalanine, tyrosine, tryptophan, arginine, or lysine. These are provided as examples of possible substitutions and are not meant to limit the scope of variations contemplated by substituting amino acids that have similar side chain properties.

In embodiments of the disclosure, the modification can include an endcap. In some of these embodiments, the endcap may be the only modification to the ordered sequence (e.g., SEQ ID NOs: 18, 19, 45, 46, 63). In other embodiments, the endcap can provide a further modification in addition to one or more other modifications as described above (e.g., SEQ ID NOs: 47, 48).

For embodiments of the disclosure that include an endcap, the endcap can provide a modification to a terminus of the peptide, such as the C-terminus or the N-term inus. Exemplary endcaps include: N-terminal acetylation (Ac-), C-terminal amidation (—$NH_2$), a protecting group, or a protein fusion. Possible protecting groups can include for example: 9-fluorenylmethoxycarbonyl (Fmoc), tert-butyloxycarbonyl (Boc), tert-butyl (t-Bu), trityl (Trt). Possible protein fusions can include: fluorescent tags, purification tags, or delivery sequences. Further, the protein fusions can include a peptide linker such as a glycine linker. Endcap modifications can assist in the delivery of the peptide to a directed site, such as a tumor cell. Endcap modifications can also assist the delivery of the peptide into the cytosol. Endcap modifications could also improve peptide stability or detection in embodiments described herein.

In some embodiments, an endcap can include a benzoic acid-based endcap. For instance, benzoic acid-based segments of the inhibitors can include an alkyl derivatives (e.g., C2-C4 or higher). In one embodiment, a N-capping group can include a benzoic-acid based group having a structure as illustrated in FIGS. 12 as N1, N2, N3, and N4.

In other embodiments, a capping group can include derivatization of a benzoic acid-based group, for instance including a C2-C5 straight chain or branched alkyl or alkyloxy linked to a benzoic acid as illustrated in the C-capping groups of FIG. 13. As illustrated, a derivatized benzoic acid capping group can include a derivatized group either ortho-, meta-, or para to the acid of the benzoic acid group. Moreover, it should be understood that derivatized benzoic acid groups as illustrated in FIG. 13 are not limited to C-capping groups and likewise, the N-capping groups of FIG. 12 can be utilized as C-capping groups in other embodiments.

Embodiments of the disclosure can include a peptide having a linear sequence. In these embodiments, the peptide having a linear sequence indicates that no intramolecular bonds exist between two different amino acids from the sequence derived from SEQ ID NO: 1. As such, a peptide having a linear sequence may include ring structures on individual residues (e.g., SEQ ID NOs: 4-15 include F515 and/or H510) but does not include cyclization bonds between peptide residues of a sequence. In particular, a linear peptide may include one or more amino acids, either as a component of a core sequence identical to a portion of SEQ ID NO: 1, or as a modification to the starting SEQ ID NO: 1 that includes a side chain ring, such as the amino acids: Histidine, Phenylalanine, Tryptophan, or Tyrosine.

Alternative embodiments of the disclosure include peptides having a cyclic sequence. In these embodiments, the peptide can include an intramolecular bond between two amino acids. Several non-limiting examples of linkages between side chains of different amino acids that can be used to produce a cyclic sequence can include a disulfide bond, a lactam ring, or a lactone ring.

In an embodiment of the disclosure, the peptide can include one or more cyclic sequences, optionally in conjunction with one or more linear sequences. Peptides that have one or more cyclic sequences can include combinations such as a disulfide bond and a lactam ring, or both cyclic sequences can include the same bond.

In some embodiments, a cyclic sequence may be deemed macrocyclic, in that a cyclic sequence of the peptide includes a ring size greater than 4 amino acid residues. In some embodiments, a cyclic sequence can include a ring size greater than 5 residues. In yet other embodiments, a cyclic sequence can include a ring size greater than 8 residues. In still other embodiments, a cyclic sequence can include a ring size greater than 10 residues.

For embodiments of the disclosure of a peptide having a cyclic sequence, in some cases the cyclic sequence can include a ring modification to adjust the ring size and/or to create a ring. As one example, the substitution of lysine for ornithine results in an additional methylene group on the amino acid side chain. Additional ring modifications can be used to adjust the ring size, such as ring closing metathesis to generate an olefin linked bridge, reductive amination to generate a secondary or tertiary amine linked bridge, and ether or thioether bridge formation. To incorporate these ring modifications, the side chains of one or more amino acids may be altered to include a reactive group. Possible reactive groups can include an alkene, a thiol, a hydroxyl, a halogen, and a nitrile.

In an embodiment, a peptide having a cyclic sequence can include an ordered sequence of amino acids corresponding to residues 504-517, 504-518, 505-518, 504-519, or 508-518 from SEQ ID NO: 1, along with a modification, for instance, in which cysteine side chains form a disulfide bond to yield a cyclic sequence.

By way of example, FIG. 9 (SEQ ID NO: 33-SEQ ID NO: 38), FIG. 12, FIG. 13, and FIG. 15 (SEQ ID NO: 50-SEQ ID NO: 62) present examples of cyclic peptides as disclosed herein. As presented, in some embodiments, a peptide having a cyclic sequence can include an ordered sequence of amino acids corresponding to residues 504-518, 504-519, 505-518, 507-518, 508-513, or 507-513 from SEQ ID NO: 1, along with one or more modifications to the SEQ ID NO: 1 residues. Modifications can include, in some embodiments, T508O and/or I513E in which the ornithine and glutamic acid side chains can form a lactam bond to yield a cyclic sequence. In another embodiment, a modification can including T508K and/or I513E in which the lysine and glutamic acid side chains form a lactam bond to yield a cyclic sequence. Substitutions of a cyclic peptide can include substitutions involved in ring formation as well as other substitutions that can affect the function of the peptide. By way of example, modifications of cyclic peptides can include, without limitation, L505C, L505O, L505Dab, L505K, T508O, T508K, R509MeR, V511P, N512A, I513E, G518E, L515hL, L515I, F516C, F516D, or any combination thereof, as well as substitution described elsewhere herein.

In one embodiment, a cyclic peptide can be based upon residues 508-513 of SEQ ID NO: 1. For instance, FIG. 12 and FIG. 13 present several cyclic peptides based upon SEQ ID NO: 48, KRHVAE, which is based upon residues 508-513 of SEQ ID NO: 1 with modifications including T508K, N512A, I513E. In one embodiment, a cyclic peptide can include SEQ ID NO: 48 with no other residues or modifications to residues of SEQ ID NO: 1. In other embodiments, a cyclic peptide can include additional residues of SEQ ID NO: 1 (or modifications thereof), which can be a component of the macrocycle or can be a linear extension of the macrocycle. For instance, FIG. 12 describes several cyclic peptides based upon SEQ ID NO: 47, which includes SEQ ID NO: 48 forming a macrocycle and residues 514-518 of SEQ ID NO: 1 (SEQ ID NO: 44, LLFMG) as a linear portion of the peptide.

For some embodiments, the peptide can include a modification to the peptide backbone. In these embodiments, the peptide can be either linear or cyclic. Additionally, the peptide can include an amino acid substitution or an endcap in addition to the modification to the peptide backbone, as well as cyclization or partial cyclization. As an example of a modification to the peptide backbone, a peptide can include an N-methylation of at least one backbone amide nitrogen, e.g., methylation of an arginine. Other modifications can include peptoid derivatives where the amino acid side chain is attached to the amide nitrogen instead of the alpha carbon.

In some embodiments, a peptide can include very few of the original peptides of SEQ ID NO: 1. For instance, in one embodiment, a peptide can have a sequence of

```
                                    (SEQ ID NO: 64)
K-MeR-a-PAE
```

which includes modifications to SEQ ID NO: 1, including T508K, R509MeR (i.e., N-methylated arginine, on the backbone amide nitrogen), H510a (i.e., a D-alanine) V511P, N512A, and I513E.

In one embodiment, a peptide can include a C2-C10 alkyl chain within the sequence, for instance, a peptide can have a sequence of K-MeR-octyl-E which includes modifications to SEQ ID NO: 1, including T508K, R509MeR, replacement of H510, V511, and N512 with an alkyl chain, in this case an octyl chain, and I513E.

The peptides disclosed herein can be synthesized using standard methods such as solid phase synthesis or an engineered cell line.

Further, the peptides disclosed herein can be included as part of a composition to maintain stability or provide a vehicle for delivery of the peptide. Example compositions having the peptide can also include carriers and/or buffers to maintain the peptide concentrations from about 0.05 μM to about 200 mM.

Embodiments of the disclosure also include methods for inhibiting growth in a target cell, such as a tumor cell, by delivering a peptide as disclosed herein to the tumor. In these embodiments, the method can include delivering a peptide as described herein to a site that contains tumor cells.

In embodiments for inhibiting growth in a tumor, the tumor can be melanoma. In other embodiments, the tumor can be hairy cell leukemia. In further embodiments, the tumor can be colorectal carcinoma. In still further embodiments, the tumor can be astrocytoma. Generally, the tumor types are not limited only to those described above. Embodiments of the disclosure can be used to inhibit growth for tumors that include a mutant RAS genotype and a mutant or a wildtype RAF genotype. Thus, embodiments of the disclosure can be used for tumors lacking the V600E mutation to B-Raf kinase.

As an example of possible RAS mutations, several amino acid positions have been identified in mutant RAS proteins present in tumors. A non-limiting list of amino acid positions for the RAS protein that may be mutant in a tumor or tumor cell using embodiments of the disclosure can include: Gly12, Gly13, and Gln61.

In any of these methods, embodiments of the disclosure can be used to inhibit growth in tumors that have demonstrated resistance to other lines of treatments, including tumors that are resistant to treatment with vemurafenib.

In an embodiment of the disclosure, the method for inhibiting growth in a tumor includes delivering a composition that includes a peptide to a patient using an administration route. In these embodiments, the administration route can include one or more of the following: Intravenous injection, intramuscular injection, oral capsule, sublingual tablet, skin ointment, or anal suppository.

In one embodiment, disclosed peptides can inhibit dimer formation between RAF kinase proteins. By inhibiting dimer formation, the methods provide a mechanism for allosterically blocking kinase function. The method for inhibiting dimer formation including exposing a RAF kinase protein to an embodiment of the composition containing a peptide where the peptide displays a binding affinity ($K_d$) to a region on the RAF kinase protein.

Another embodiment of the disclosure is a method for inhibiting dimer formation between RAF kinase proteins. In some embodiments, the RAF kinase protein can be present in a tumor cell, such as a melanoma cell, and in one particular embodiment, in a metastatic melanoma cell. In other embodiments, the RAF kinase protein can be isolated from a cell such that the RAF kinase protein is in solution. In these embodiments, the RAF kinase protein can include B-Raf kinase.

In embodiments of the disclosure that provide a method for inhibiting dimer formation between RAF kinase proteins, the RAF kinase proteins can include a mutation. Mutations are common in cancer cells, and the peptides and compositions described herein can be used to inhibit dimerization between RAF kinase proteins that display a mutation. In an exemplary embodiment, the method for inhibiting dimer formation can include delivering a peptide or a composition containing a peptide to a B-Raf kinase protein. For these embodiments, the B-Raf kinase protein can include a V600E point mutation.

In embodiments of the disclosure, the peptide binding affinity $K_d$ for the dimer interface can be approximately 3.50 μM or less. In certain embodiments, the binding affinity $K_d$ can be approximately 2.00 μM or less. In some embodiments, the binding affinity $K_d$ can be approximately 1.00 μM or less, such as about 0.75, about 0.70, about 0.65, about 0.60, about 0.55, or about 0.50 μM or less. In an exemplary embodiment, the binding affinity $K_d$ can be approximately 0.1 μM or less.

In any of the above embodiments, the peptide may include a REPLACE modification to replace residues in the peptide for non-peptidic analogues and/or to provide capping groups for a peptide. For example, the REPLACE modification could be applied to the residues of a peptide that conform to residues of the reference sequence SEQ ID NO: 1. Alternatively, or additionally, the REPLACE modification could be applied to residues that are modified compared to SEQ ID NO: 1. The REPLACE modification utilizes structure-activity relationships to substitute a nonpeptide fragment for portions of a peptide inhibitor, as illustrated in U.S. Pat. No. 9,175,357, incorporated in its entirety herein by reference. By utilizing computational analysis, the REPLACE strategy provides a mechanism to identify nonpeptide fragments which display similar, improved, or diminished binding and/or interactions as the peptide fragment that is being replaced. The fragment can be developed to substantially maintain and mimic the structure activity in an analogous manner to the substitution of an amino acid having a hydrophobic side chain for different amino acids with a hydrophobic side chain, except without being constrained to using an amino acid. Using this method, each potential nonpeptide fragment can be scored and thus prioritized through energetic and/or geometric evaluation of computational docking simulations.

Some examples of nonpeptide fragments can be found in U.S. Patent Pub. 2017/0283445, incorporated in its entirety herein by reference. Generally, these fragments include an aromatic core that can be heterocyclic and includes at least one substitution to the ring. Other fragments can include secondary or tertiary amines that include an alpha, beta, or gamma carboxyl group.

An exemplary nonpeptide fragment can include the following structure,

Structure I:

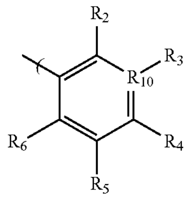

in which $R_2$-$R_6$ are independently selected from hydrogen, carboxyl, alkyl, alkyl ester, hydroxyl, methoxy, halogen, amino, alkylamino, thiol, thioalkylether, sulfonamide, phosphate, nitro, methylamine, or boronic acid, and $R_{10}$ is C or N, and $R_3$ is relevant only when $R_{10}$ is C.

Several non-limiting structures for nonpeptide fragments derived from Structure I are included below as Structures Ia-Id:

Ia

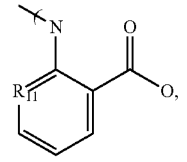

$R_{11}$ = CH, N

Ib

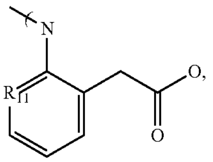

$R_{11}$ = CH, N

Ic

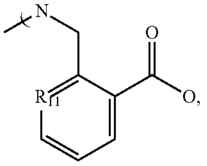

$R_{11}$ = CH, N

Id

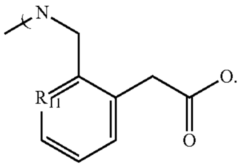

$R_{11}$ = CH, N

Another exemplary nonpeptide fragment can include the following structure,

Structure II:

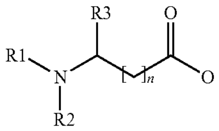

in which R1, R2, and R3 are selected from a hydrogen (H) or an alkyl group having a chain length of 1-3 carbons and n=0-3.

Several non-limiting structures for nonpeptide fragments derived from Structure II are included below as Structures IIa-IIb:

IIa

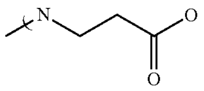 and

IIb

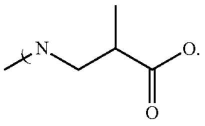

Another exemplary nonpeptide fragment can include the following structure, Structure III:

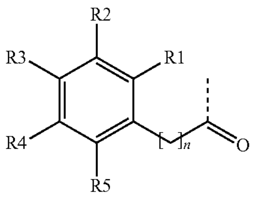

in which R1-R5 can be independently selected from a hydrogen (H), a linear or branched alkyl group having a chain length of 1-5 carbons, an amine, aminoalkyl, thiol, thioalkylether, an amide, a carboxylate, a sulfate, a sulfamide, a cyano, or a halogen (e.g., F, Cl, or Br), and n=0-4.

Several non-limiting structures for nonpeptide fragments derived from Structure III are included below as Structures IIIa-IIId:

IIIa

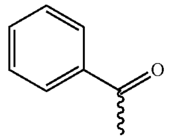

IIIb

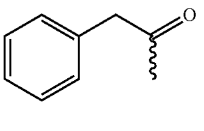

IIIc

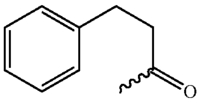

IIId

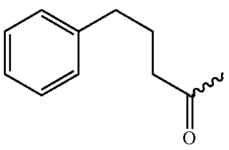

Another exemplary nonpeptide fragment can include the following structure, Structure IV:

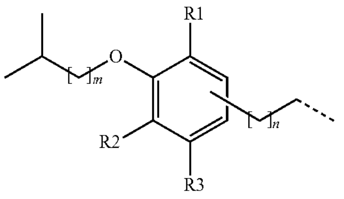

in which R1-R3 can be independently selected from a hydrogen (H), a linear or branched alkyl group having a chain length of 1-5 carbons, an amine, an amide, a carboxylate, a sulfate, a sulfamide, a cyano, or a halogen (e.g., F, Cl, or Br); and the alkyl chain having a chain length, n=0-3, may be positioned on the phenyl ring at any position including ortho, meta, or para, relative to the alkoxy group having a chain length, m=1-5.

Several non-limiting structures for nonpeptide fragments derived from Structure IV are included below as Structures IVa-IVc:

IVa

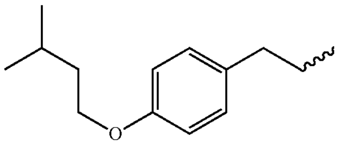

IVb

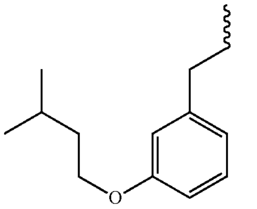

IVc

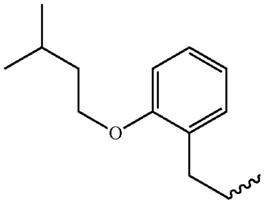

A further example nonpeptide fragment that can be incorporated in embodiments of the disclosure can include the following structure, Structure V:

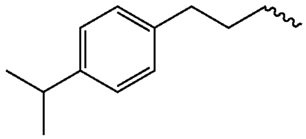

In an example implementation of the REPLACE strategy, SEQ ID NO: 38 can include substituting the sequence of amino acid residues LRK (SEQ ID NO: 49) with a nonpeptide fragment having the general structure of Structure III as N-caps and including SEQ ID NO: 47, with a portion of the sequence, SEQ ID NO: 48, as a macrocyclic portion of the peptide and a portion of the sequence, SEQ ID NO: 44, as a linear portion of the peptide. Certain characteristics for embodiments using Structures IIIa-IIId as N-capping groups and NH2 as a C-capping group are shown in FIG. 12.

In another example implementation of the REPLACE strategy, SEQ ID NO: 38 can include substituting the sequence of amino acid residues LLFMG (SEQ ID NO: 44) with a nonpeptide fragment having the general structure of Structure IV as C-caps of the peptide. Certain embodiments using Structures IVa-IVc as C-capping agents are shown in FIG. 13, with the peptide including SEQ ID NO: 48 as a macrocyclic portion of the peptide, and a portion of the sequence, LRK (SEQ ID NO: 49), as a linear portion of the peptide, and including an N-terminal acetylation as a capping group.

Generally, implementations of the REPLACE strategy can be used to replace a single amino acid residue or may be combined by substituting one or more sequences of amino acids with nonpeptide fragments. For example, any embodiment of the disclosure or any of the peptide sequences disclosed herein that include amino acid residues LRK (SEQ ID NO: 49), LLFMG (SEQ ID NO: 44), or both (e.g., in any of SEQ ID NOs: 31-38) can include a REPLACE modification to substitute one or both sequences of amino acid residues LRK (SEQ ID NO: 49) and LLFMG (SEQ ID NO: 44), respectively, with a first nonpeptide fragment having the general structure of Structure III and/or a second nonpeptide fragment having the general structure of Structure IV.

As another example implementation of the REPLACE strategy, SEQ ID NO: 31 can include a REPLACE modification to substitute one or both sequences of amino acid residues LRK (SEQ ID NO: 49) and LLFMG (SEQ ID NO: 44), respectively, with a first nonpeptide fragment having the general structure of Structure III (e.g., Structure IIIa) and a second nonpeptide fragment having the general structure of Structure IV (e.g., Structure IVa). Certain attributes, including $K_d$ values, for exemplary peptide-based inhibitors designed in accordance with the disclosure are shown in FIG. 14, which include the resulting sequences, i.e., SEQ ID NO: 17, 45, 46, 48, 62, 63, 64 with or without various capping groups, as shown. The C-terminal capping groups were designed in these samples to take advantage of the dep hydrophobic pocket of L515, while the N-terminal capping groups were designed to exhibit pi-stacking interactions with W450 BRAF residue.

As shown in FIG. 1, peptides as disclosed herein can display a binding affinity to the dimer forming interface of B-Raf. The unmodified starting sequence, SEQ ID NO: 1, displays a $K_d$ of 3.84±0.32. As shown, some peptides exhibit a lower value to about 0.54, (SEQ ID NO: 6) and other peptides exhibited no measurable binding (SEQ ID NO: 2, SEQ ID NO: 9, and SEQ ID NO:14).

FIG. 2A displays Western blot gels demonstrating that the addition of the inhibitory peptides based on SEQ ID NO: 1 and SEQ ID NO: 17 to NRASQ61K-mutant SBcl2 melanoma cells can reduce downstream signaling of MEK and ERK by lowering the amount of the phosphorylated or activated form of these proteins (pMEK and pERK). In FIG. 2A, cells were electroporated with the BioRad Gene Pulser XCell™ in the presence of the indicated concentrations of SEQ ID NO: 1. Following recovery at 37° C. for 30 minutes, the cells were treated with 1 μM PLX4032 for 1 hour or DMSO as a vehicle control. Subsequently, the cells were harvested, lysed using RIPA buffer and analyzed by Western blotting using the indicated antibodies. In FIG. 2B, NRASQ$^{Q61K}$ mutant human SBC12 melanoma cells were incubated with 3.60 μM of FAM-TAT-Pep6AlaNC3 (as control, GVLAATAAVNALLFAGYST, SEQ ID NO: 68) or FAM-TAT-SEQ ID NO: 17 for three days (TAT-GRKKRRQRRR-(PEG2), SEQ ID NO: 69). Four hours prior to harvest, the cells were treated with 1 μM vemurafenib (PLX4032), or the same volume of DMSO as vehicle control. RIPA buffer lysates were subjected to Western blotting using the indicated antibodies. Detection of Hsp90 served as a representative loading control. Note that vemurafenib (PLX4032) upregulated the expression and phosphorylation of MEK, ERK, and its target FRA1 in FAM-TAT-Pep6AlaNC3 treated control cells, while this response was not observed in the presence of FAM-TAT-SEQ ID NO: 17.

In addition, the SEQ ID NO: 68 control peptides were taken up by cells treated with higher concentrations, whereas treatment with lower concentrations of the control peptides provided only a diffuse autofluorescence in the wells. Cells treated with the SEQ ID NO: 17 (i.e., FAM-TAT-SEQ ID NO: 17) test sequence formed smaller colonies and were round in nature, compared to the larger colonies with elongated cells treated with the negative control (results not shown). The results indicated that the test sequence impaired SBcl2 melanoma cell growth at 1.8 μM with no colonies formed when treated at 3.6 μM. In addition, the control sequence (SEQ ID NO: 68), impaired cell growth at 7.2 μM, a 4-fold greater concentration, indicating a binding requirement of the side chains contacting the DIF binding surface.

Figure 3A:
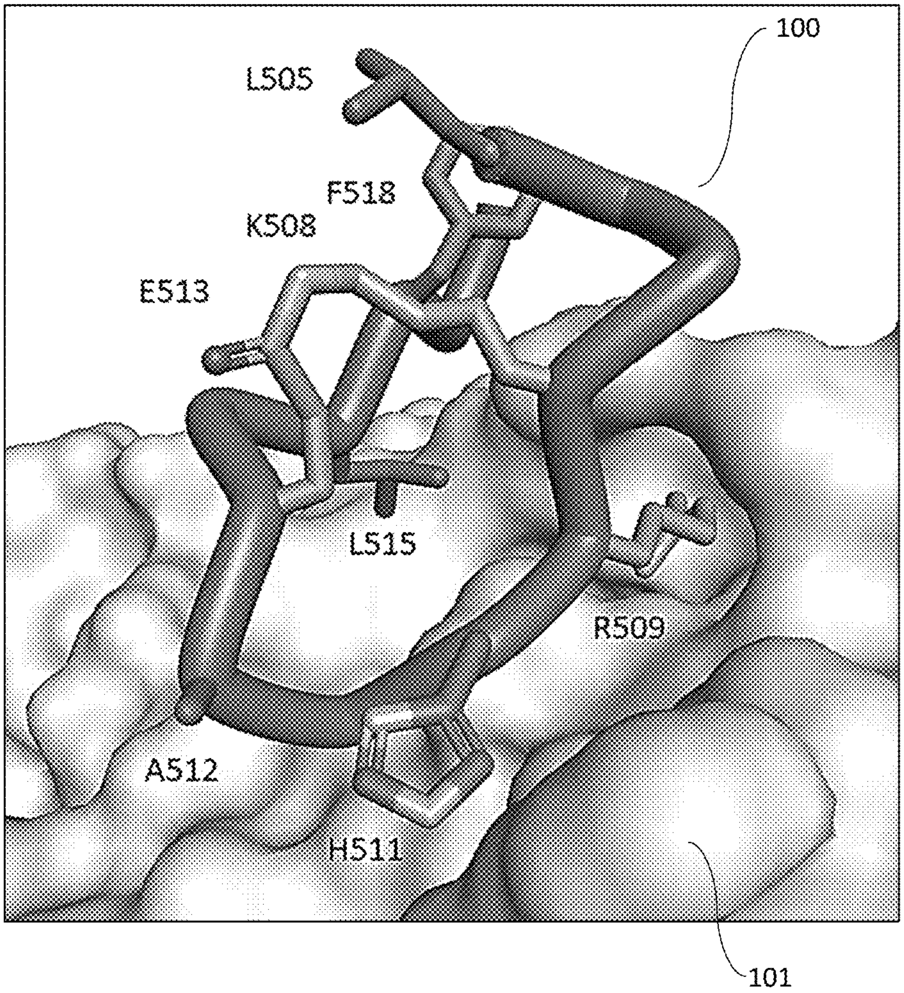
FIG. 3A illustrates the structure of SEQ ID NO: 38 bound to B-Raf.

FIG. 3A illustrates the structure of SEQ ID NO: 38 100 bound to B-Raf 101. The major binding residue R509, small cyclization site (508-513), and large cyclization site (505-516) are indicated. Other residues for interaction with B-Raf are labeled including H510, A512 and L515.

Figure 3B:
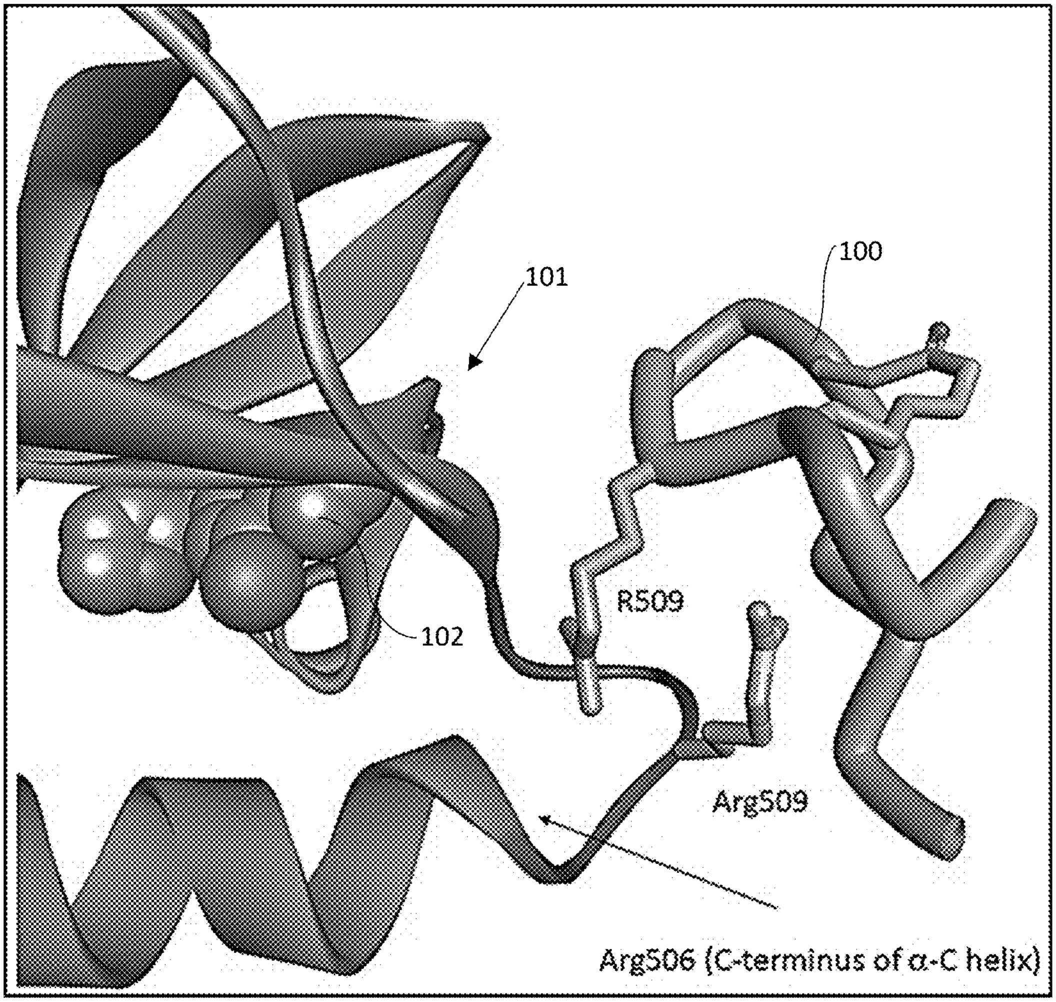
FIG. 3B illustrates the Dimer Interface (DI) showing the interaction between the SEQ ID NO: 38 and B-Raf. R509 (peptide) forms an antiparallel binding mode with Arg509 (B-Raf) as observed from the crystal structure.

FIG. 3B shows the dimer interface, illustrating the interaction between the peptide SEQ ID NO: 38 100 and B-Raf 101. Peptide residue R509 forms an anti-parallel binding mode with Arg509 (B-Raf) as observed from the crystal structure. It is proposed that the charge-charge repulsion of the two guanidinium groups is offset by the interaction of the positive charge with the negative charge on the C-terminal end of the α-C helix created by the helix dipole. A space-filling representation of the ATP competitive kinase inhibitor 102 (from 4E26) indicates the proximity of the dimer forming interface to the catalytic site.

Figure 4:
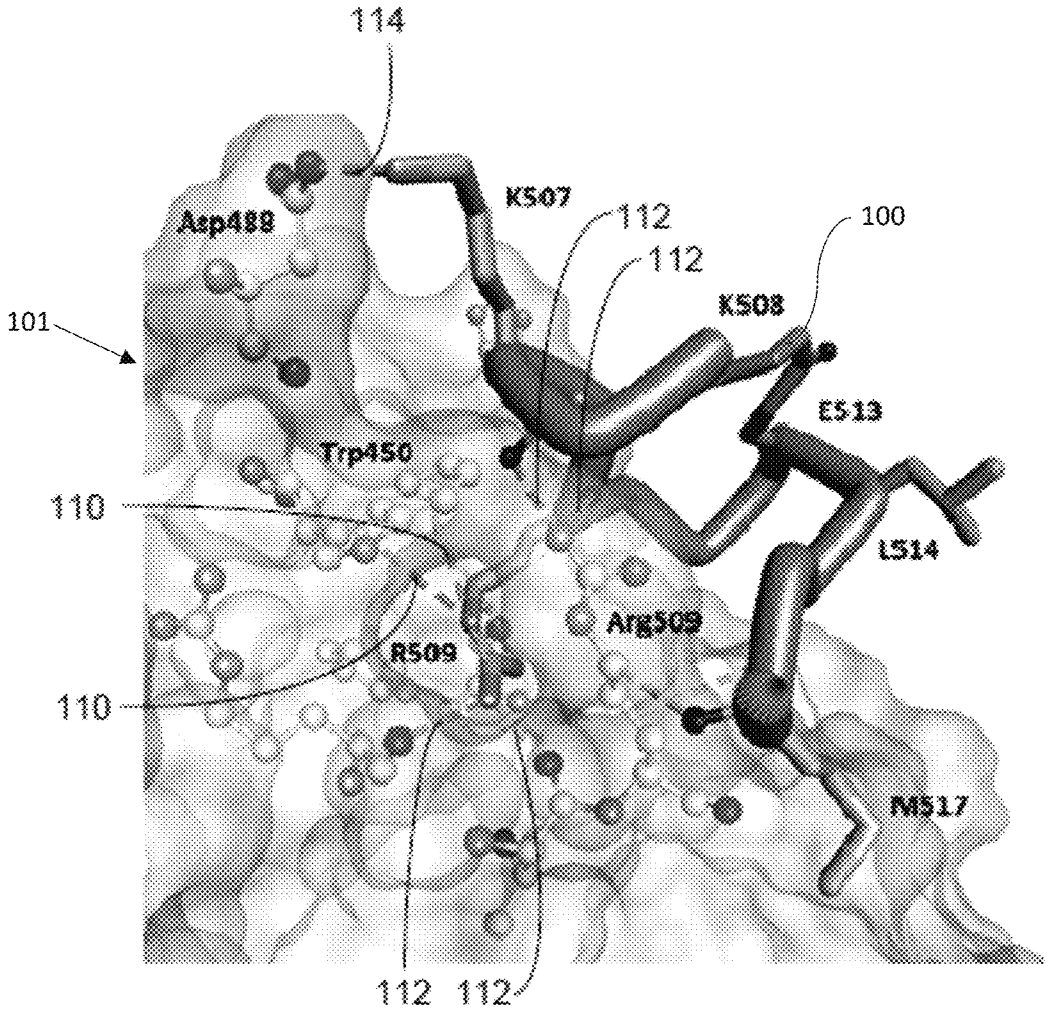
FIG. 4 illustrates some of the binding interactions between residues of an example peptide inhibitor and B-Raf residues.

FIG. 4 illustrates a view of the bound SEQ ID NO: 38 100 (one letter residue codes) with B-Raf 101 (three letter residue codes) and illustrating some predicted stabilizing non-bonded interactions. The predicted interactions include Pi-cation 110, H-bond 112 and salt bridge 114, shown as dashed lines.

Figure 5:
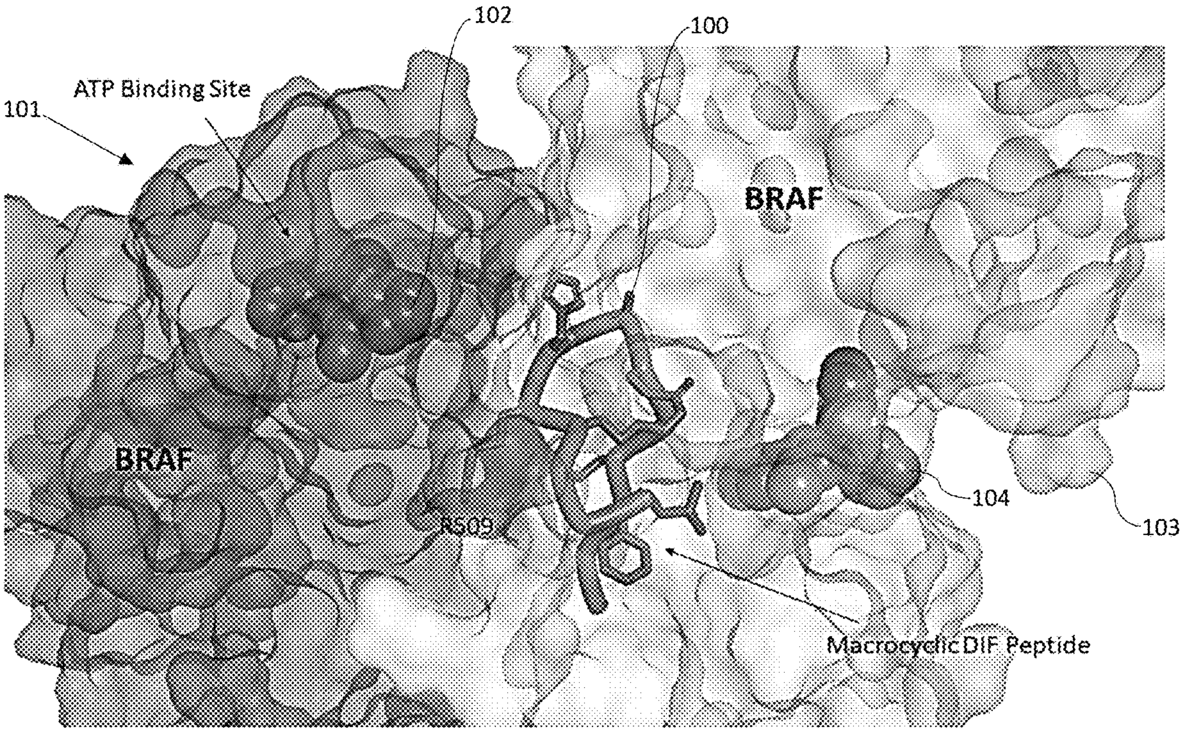
FIG. 5 illustrates a macrocyclic dimer interface inhibitor between two B-Raf kinase proteins.

FIG. 5 illustrates a B-Raf kinase protein dimer with SEQ ID NO: 38 100 at the interface. A B-Raf kinase protein 101 is shown with the kinase inhibitor 102, shown as space-filled representation. A second B-Raf kinase protein 103 is also shown with a second kinase inhibitor 104.

Figure 6:
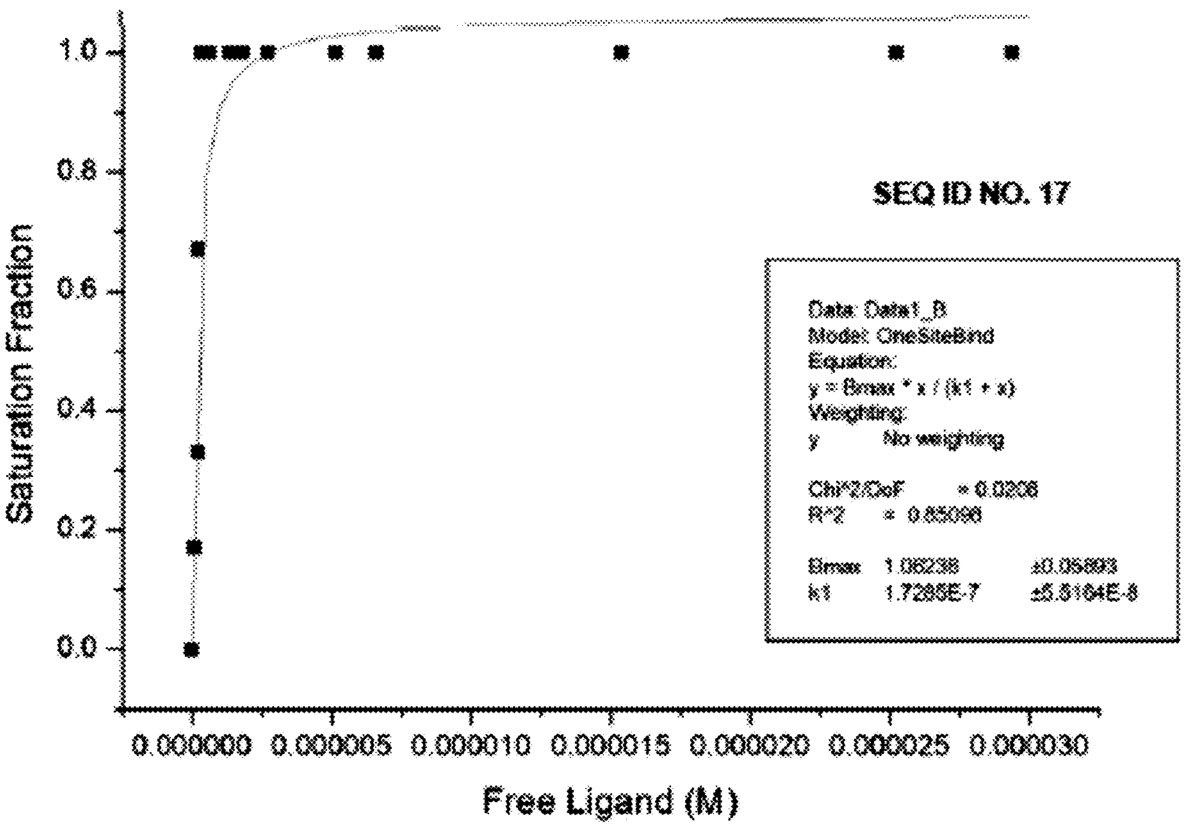
FIG. 6 illustrates a graph displaying saturation fraction versus free ligand (M) using the SEQ ID NO: 17.

FIG. 6 illustrates a graph showing a saturation binding curve obtained for binding of SEQ ID NO: 17 to B-Raf using intrinsic Trp fluorescence.

Figure 7:
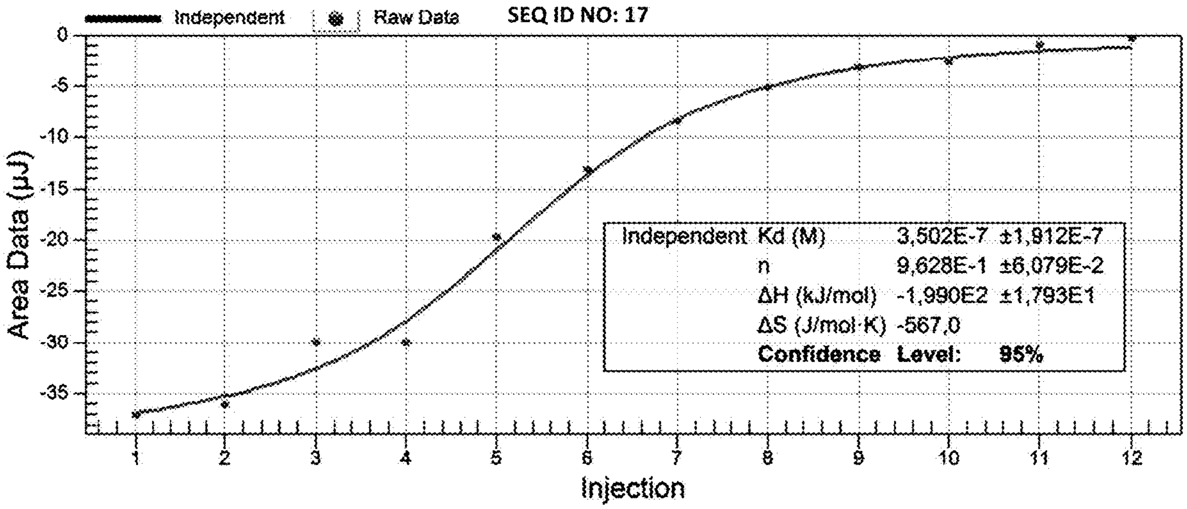
FIG. 7 illustrates a graph of raw data and an independent fit line displaying area data versus injection using SEQ ID NO: 17.

FIG. 7 shows a binding curve for peptide SEQ ID NO: 17 to B-Raf using Isothermal Titration Calorimetry ("ITC"). ITC is an analytical method of quantifying the change in temperature per addition of ligand to a biological system, to where loss of change in temperature indicates ligand saturation and a $K_d$ can be obtained. Knowing the energy released and the temperature at equilibrium allows for the determination of ΔH and ΔS, where a negative ΔH and a positive ΔS are favorable and lead to a spontaneous binding, as ΔG=ΔH−TΔS. Table 1, below, compares values obtained for binding affinities according to two different techniques (ITF and ITC), change in enthalpy, and change in entropy for three representative peptides.

TABLE 1

| SEQ ID NO | ITF $K_d$ (μM) | ITC $K_d$ (μM) | ΔH (kJ/mol) | ΔS (kJ/mol) |
|---|---|---|---|---|
| 8 | 2.8 | 14.9 ± 10.8 | −34.8 | −28.4 |
| 17 | 0.13 | 0.35 ± 0.17 | −199.0 | −567.0 |
| 36 | 0.46 | 0.31 ± 0.16 | −9.4 | 92.1 |

FIG. 8 describes additional peptide inhibitors that can also display a binding affinity for the dimer forming interface. The peptides can include a modification such as an amino acid substitution (SEQ ID NO: 20 through SEQ ID NO: 30) or an endcap (SEQ ID NO: 18, SEQ ID NO:19) that can improve or adjust the binding affinity for the dimer forming interface.

FIG. 9 describes additional peptides that can include a macrocyclic presentation. As indicated, the macrocyclic examples of FIG. 9 can display a binding affinity for the dimer forming interface. The peptides can include at least 2 amino acid substitutions and a side chain bond such as a disulfide bond (SEQ ID NO: 33) or a lactam ring (SEQ ID NO: 34 through SEQ ID NO: 38) to produce the macrocyclic ring.

FIGS. 10A and 10B display tables that indicate LCMS conditions and results for analyzing peptides described in embodiments herein.

Figure 11A:
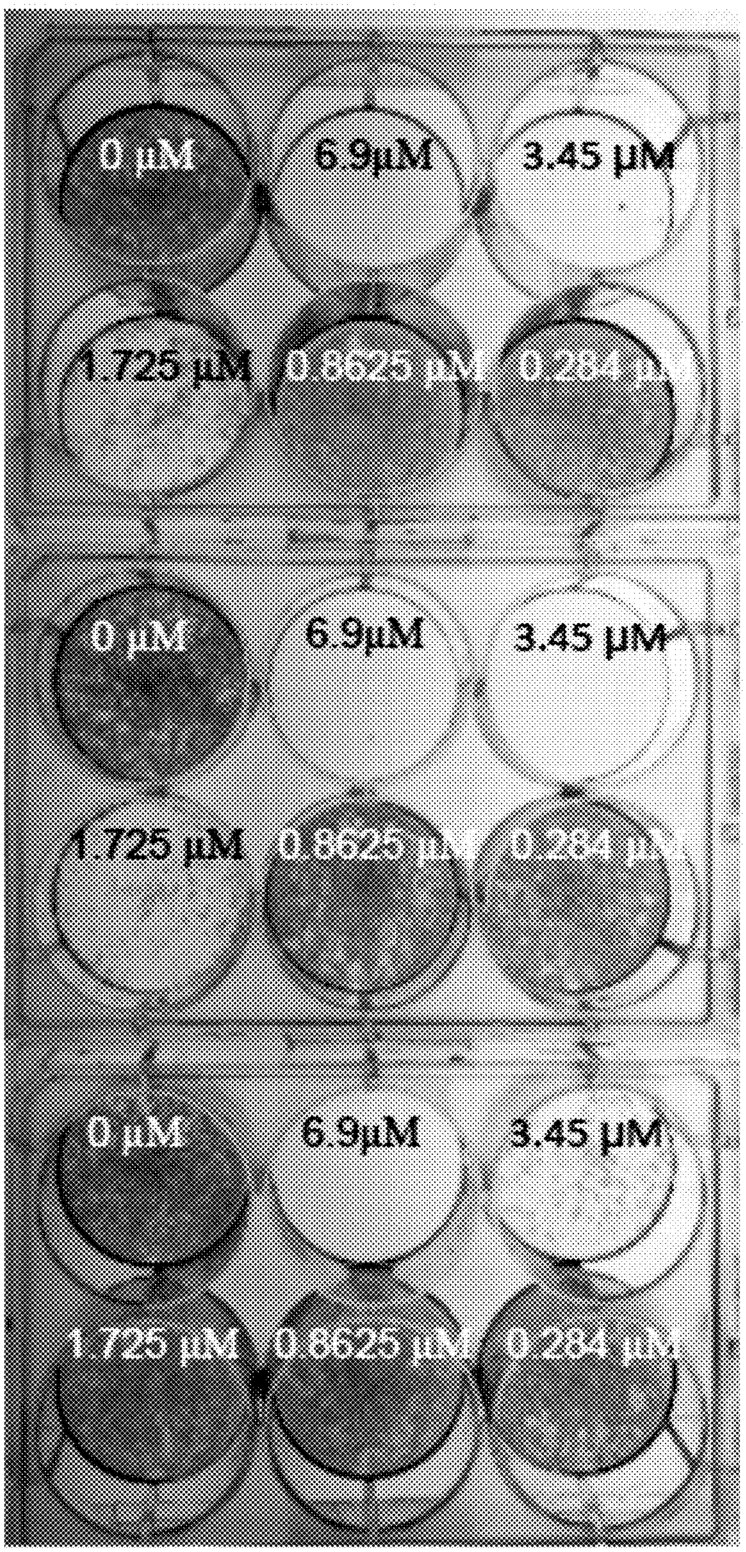
FIG. 11A illustrates images of a well plate assay using exemplary embodiments of the disclosure.
Figure 11B:
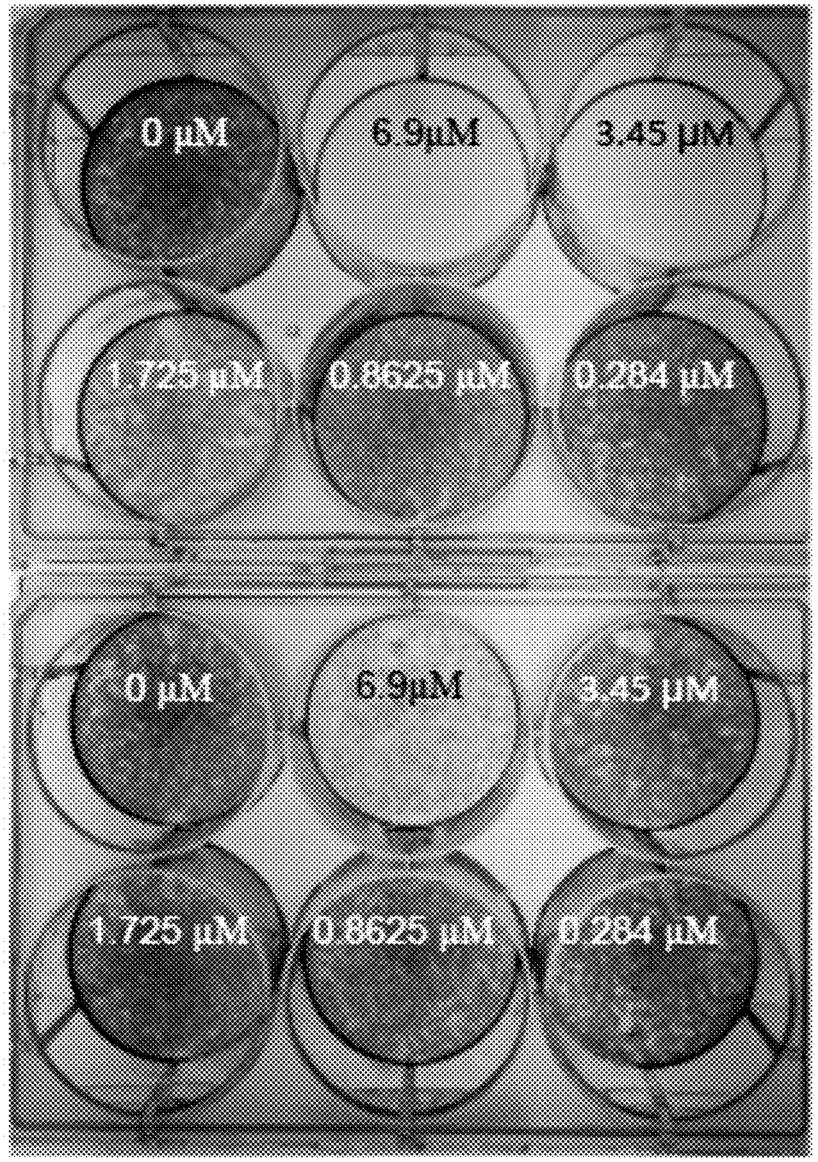
FIG. 11B illustrates images of another well plate assay using exemplary embodiments of the disclosure.

FIGS. 11A and 11B illustrate a well plate assay demonstrating the effect of embodiments of the disclosure on the growth of melanoma cells. Several example peptides corresponding to SEQ ID NOs: 1-3 (Peptide I-III, respectively) were provided to melanoma cells at concentrations of the peptide inhibitor ranging from 0 μM to about 6.9 μM. In the images, a darker or opaquer well indicates that cell growth was less inhibited, and a lighter or clearer well indicates that cell growth was more inhibited. Going from left to right and top to bottom of FIG. 11A and FIG. 11B, the six wells of each assay included respective concentrations of the indicated peptide of 0 μM, 6.9 μM, 3.45 μM, 1.725 μM, 0.8625 μM, 0.284 μM.

FIGS. 12 and 13 present representative cyclic peptides and include data for each structure. In FIG. 12, the peptide inhibitor having the sequence corresponding to KRHVAELLFMG (i.e., SEQ ID NO: 47) includes a modification to include an N-Capping group as shown on the ring structure (i.e., KRHVAE, SEQ ID NO: 48), as well as an amine cap at the C-terminal of the linear portion of the peptide (i.e., LLFMG, SEQ ID NO: 44). Also shown are the corresponding interaction energy (IE) and capping group contributions to the IE. For these embodiments, the IE is generally shown to decrease compared to the control peptide (i.e., KKRHVAELLFMG, SEQ ID NO: 66), indicating more favorable binding of the modified peptides, though, as shown in FIG. 13, some capping groups may cause the IE to increase. In FIG. 13, the peptide inhibitor having the sequence LRKKRHVAE (SEQ ID NO: 67), which includes the ring structure of SEQ ID NO: 48 and a linear sequence LRK (SEQ ID NO: 49), also includes an N-terminal acetylation in conjunction with a C-capping group, as shown. As shown, embodiments of the REPLACE modification can include structures that decrease the IE (e.g., Structures IVa-c) and/or structures that increase the interaction energy (e.g., Structure V). Generally, the more negative the IE, the lower the $K_d$, and thus, the more tightly bound the modified peptide.

Cyclization of various peptides as described in Table 2, below, was carried out and the binding affinity for each with BRAF was determined and compared to two linear peptides (SEQ ID NO: 17 and SEQ ID NO: 31), as shown. In Table 2, the residues of the cyclization reaction are in bold. As indicated, SEQ ID NO: 53, with cyclization occurring via reaction between the modified residues T508K and I513E demonstrated the highest binding affinity.

TABLE 2

| SEQ ID NO: | Sequence | $K_d$ (μM) |
|---|---|---|
| 17 | VLRKTRHVNILLFMG | 0.13 ± 0.040 |
| 16 | VLRKTRHVNILLFM | 5.75 ± 1.2 |
| 33 | V**C**RKTRHVNILL**C**M | 0.36 ± 0.32 |
| 50 | V**K**RKTRHVNILLFM**E**Y | INS |
| 51 | V**O**RKTRHVNILLFM**E**Y | INS |
| 52 | VLRK**O**RHVN**E**LLFMG | 0.78 ± 0.10 |
| 53 | VLRK**K**RHVN**E**LLFMG | 1.89 ± 0.33 |
| 54 | VDabRK**K**RHVN**E**LLDMG | 0.37 ± 0.03 |
| 55 | VLRKORHVAELLFMG | NB |

A modified cyclic peptide library was developed to compare several modifications, include examination of a lactam bridge for cyclization (e.g., T508O vs. T508K), a decrease in the number of amide backbone HBDs (e.g., methylation of R509), inclusion of proline to examine possible stabilization of the reverse-β-turn conformation), reduction of size, HBDs and HBAs in the cyclic context (e.g., N512A), optimization of the hydrophobic pocket binding (e.g., L515 modification), and reduction of the overall size and polarity of a cyclic peptide as well as priming the peptides for optimization via REPLACE (e.g., C-, N-truncation). The cyclic peptides and determined binding affinities are shown and compared with two linear peptides in Table 3, below. The residues of the cyclization reaction are shown in bold in the table.

TABLE 3

| SEQ ID NO: | Sequence | $K_d$ (μM) |
|---|---|---|
| 17 | VLRKTRHVNILLFMG | 0.13 ± 0.040 |
| 31 | LRKTRHVNILLFMG | 1.88 ± 0.36 |
| 52 | VLRK**O**RHVN**E**LLFMG | 0.78 ± 0.10 |
| 53 | VLRK**K**RHVN**E**LLFMG | 1.89 ± 0.33 |
| 55 | VLRK**O**RHVA**E**LLFMG | 0.46 ± 0.04 |
| 57 | VLRK**O**RHVA**E**LhLFMG | 0.43 ± 0.03 |
| 58 | VLRK**O**RHVA**E**LIFMG | 0.17 ± 0.06 |
| 59 | VLRK**K**RHVA**E**LLFMG | 0.061 ± 0.01 |

TABLE 3-continued

| SEQ ID NO: | Sequence | $K_d$ (μM) |
|---|---|---|
| 60 | VLRK**K**MeRHVA**E**LLFMG | 0.039 ± 0.02 |
| 47 | **K**RHVA**E**LLFMG | 0.59 ± 0.02 |
| 61 | **K**RHPA**E**LLFMG | 0.16 ± 0.02 |
| 48 | **K**RHVA**E** | 0.30 ± 0.03 |

Overall, the T508-I513 cyclization site I513 cyclization site demonstrated as a desirable site for development of a more drug-like macrocyclic peptide by reducing the overall size of the macrocycle. In addition, it appears that cyclization of DIF peptides entropically drives binding due to decrease in flexibility by restricting the peptide to its bioactive conformation as exemplified by ITC determination of a positive ΔS of binding (Table 1). SEQ ID NO: 59 provided a high potency ($K_d$=61 nm) when cyclized through K508-E513 and paired with the N512A mutation. Truncation of the exocyclic sequences to form SEQ ID NO: 48 resulted in minimum binding affinity loss while minimizing the overall size, which can provide permeability improvement. Results demonstrate that cyclizing the peptide can be utilized to maintain the bioactive secondary structure and decrease the entropic cost of binding.

Exemplary peptides were also examined for physiochemical properties with regard to oral bioavailability of the peptides. General guidelines for bioavailability included the following:

MW—500-1300 Da

HBD—1-6

HBA—5-20

Log P—1-8

RotB—5-20 tPSA<300 $Å^2$

Results are shown in Table 4, below. As can be seen, the physiochemical properties of the examined peptides improved through SEQ ID NO: 48.

TABLE 4

| SEQ ID NO: | Type | N-Cap/ C-Cap | MW (g/mol) | HBD | HBA | cLogP | tPSA |
|---|---|---|---|---|---|---|---|
| 1 | Linear | None | 2205.66 | 28 | 26 | N/A | 885 |
| 38 | Cyclic | None | 1679.12 | 20 | 18 | −2.34 | 651 |
| 47 | Cyclic | None | 1281.59 | 15 | 14 | −1.06 | 476 |
| 61 | Cyclic | None | 1278.7 | 14 | 14 | −1.50 | 467 |
| 48 | Cyclic | None | 719.85 | 10 | 9 | −3.94 | 330 |
| 63 | Linear | N2/C4 | 1032.26 | 11 | 12 | 0.98 | 363 |
| 48 | Cyclic | N1/C2 | 1014.24 | 10 | 11 | 1.94 | 328 |
| 64 | Cyclic | N1/C2 | 960.19 | 7 | 10 | 3.13 | 286 |
| 65 | Cyclic | N1/C2 | 862.13 | 6 | 7 | 3.71 | 237 |

A parallel artificial membrane permeability assay (PAMPA) was carried out using phospholipid and dodecane as the artificial membrane. Peptides examined by the assay included SEQ ID NOs: 1, 38, 48, 64, and 65. For all compounds, there was no detectable trace of passive permeability as determined by mass spectroscopy.

As demonstrated herein, N- and C-capping groups can simultaneously bind and synergistically increase binding affinity of the peptides. In addition, backbone amide protons appear to not be involved in IMHBs under lipophilic conditions and N-methylation can thus be used reduce the number of HBDs for enhanced cell permeability. Compared to the reference SEQ ID NO: 1, disclosed peptides, e.g., SEQ ID NO: 64, have significantly enhanced physiochemical properties for passive cell permeability, and though cell permeability has not yet been demonstrated, SEQ ID NO: 64 has a 225-fold increase in direct binding affinity compared to SEQ ID NO: 1.

The present disclosure may be better understood with reference to the Methods set forth below in combination with the Figures.

Methods

Solid Phase Synthesis of Linear Peptides

The synthesis of peptide analogs was accomplished using standard Fmoc chemistry. The linear sequences were synthesized on H-Rink Amide ChemMatrix® resin using a Protein Technologies Prelude peptide synthesizer. Initially, the resin was swelled in DMF 3 times followed by 5-minute washes. Amino acid coupling reactions were accomplished with Fmoc-protected amino acids (4 eq), HATU (4 eq), and DIPEA (8 eq), the reagents were dissolved in DMF (5 mL) and the reaction was mixed via nitrogen bubbling for 2 hours at room temperature. Following coupling, the reaction vessel was drained, and the resin is washed 3× with DMF, 3× with DCM, and 3× with DMF again. For Fmoc deprotection, the resin is treated with a solution of piperidine (20% in DMF) 2×10 minutes. Again, the resin is washed as previously stated and the process is repeated for each respective residue in the defined sequence.

Peptide Cyclization Reactions

Side chain to side chain cyclization was accomplished by one of two methods, either through a lactam linkage or through a disulfide bond linkage. Cyclization residues with orthogonal protecting groups were chosen to be able to selectively deprotect the side chains of specific residues without affecting the rest of the peptide. For the lactam method, the amine residue's side chain was protected with Mtt and the acid residue's side chain was protected with 2-O-PhiPr. Both protecting groups can easily be removed by treatment (7×3 minutes) of the resin with a low concentration of TFA (2%) in DCM. Once the orthogonal protecting groups were removed, overnight treatment with HATU (4 eq) and DIPEA (8 eq) was used to effectively cyclize the linear, partially deprotected peptide. For the disulfide cyclized peptides, the cysteine residues involved in the cyclization were orthogonally protected with Mmt, which can easily be removed by treatment (7×3 minutes) of the resin with a low concentration of TFA (2%) in DCM. Following deprotection, the two cysteine side chains were oxidized to form the disulfide bridge by treatment with a solution of NCS (2 eq) dissolved in DMF for 15 minutes at room temperature. Following cyclization, peptides were cleaved from the resin by treatment with a solution of TFA/TIPS/H2O (94/5/1) for two hours. The cleavage solution was drained from the synthesis vessel and the solvent evaporated to yield the crude product.

N-terminal Capped Peptide Synthesis

Peptides were synthesized on H-Rink Amide ChemMatrix® resin using standard Fmoc chemistry as previously stated. After the linear sequence was complete, the terminal Fmoc protecting group is removed by treatment (2×10 minutes) with a solution of piperidine (20% in DMF). Following deprotection, the resin is washed three times each with DMF, DCM, and DMF again. For the addition of the capping group, the resin is treated with a solution of the N-terminal capping group (4 eq), HATU (4 eq), and DIPEA (8 eq) dissolved in DMF for 2 hours while shaking at room temperature. The resin is then washed three times each with DMF and DCM. If the peptide is to be cyclized, that procedure would happen here using methods stated previously, and if not, the peptide is cleaved from the resin as previously stated.

C-terminal Capped Peptide Synthesis

Peptides were synthesized on 2-chlorotrityl chloride resin using standard Fmoc chemistry as previously stated. After the linear sequence was complete, the peptide was cyclized if need be, then the peptide was cleaved under mild conditions by treatment (2×5 minutes) with a solution of TFA (1% in DCM). The solution was then collected, and the solvent was removed via evaporation to yield the protected peptide in solution with a free C-terminus carboxylic acid. For the addition of the capping group, the protected peptide is dissolved in DCM and treated with a solution containing the C-terminal capping group (2 eq), HATU (2 eq), and DIPEA (4 eq), all dissolved in DCM and allowed to stir at room temperature overnight. The reaction was ended by evaporation of the solvent and then treatment with a solution of TFA/TIPS/$H_2O$ (94:5:1) for 2 hours for the removal of the protecting groups. The solvent was then removed by evaporation and the product is then ready for purification.

Purification of Cyclic Peptides

The crude peptide product was precipitated several times from cold ethyl ether and filtered through a fritted funnel to remove the majority of the scavenged protecting groups. The precipitate was then dissolved in a solution of ACN/MeOH/$H_2O$ (1:1:1) and further purified by 200 μL injections onto a Phenomenex® C18 semi-preparative column. Separation was accomplished using a standard water/acetonitrile (0.1% formic acid) mobile phase with a separation gradient of 5-30% B over 40 minutes. Fractions were characterized via mass spectrometry, combined, and purity evaluated by injection on an analytical LCMS column.

Dissociation Constant ($K_d$) Determination from Fluorescence Measurements

The dissociation constant is an indicator of binding strength between two molecules. For the reaction: P+L⇋PL $K_d$ is expressed by Equation 1:

$$K_d = [P][L]/[PL] \quad \text{Eq. 1}$$

where [P] is the concentration of free Protein, [L] is the concentration of free Ligand, and [PL] is the Ligand-bound-Protein. Eq. 1 indicates that $K_d$ is inversely related to the concentration of the Ligand-bound-Protein.

Fluorescence intensity was measured with a Hitachi F-2500 Fluorescence Spectrophotometer. A 1.6 mL of protein solution (0.5 μM) was placed in a cuvette and equilibrated at 15° C. for 1 hour. After equilibration, small increments (2-15 μL) of the ligand solution were injected in the cuvette. The experiments were performed in 20 mM HEPES buffer (pH 7.5), 10 mM MgCl2, 30 mM NaCl. (For certain ligands that were insoluble in aqueous media, 5-10% DMSO was added to increase ligand solubility). The excitation and emission wavelengths were 274 nm and 304 nm respectively. The slits were set at 10 and 10 nm in the excitation and emission respectively. To determine dilution effect of B-Raf (due to ligand addition) and any fluorescence effect by unbound ligand, a blank sample containing Trp with the same fluorescence signal was titrated with ligand additions as described above. The sample absorbance was kept below 0.1 to minimize the inner filter effect.

Dissociation constant of B-Raf/Ligand was calculated by fitting data in Eq. 2.

$$[L_{total}] = \frac{2\Theta[P_{total}]}{K_b\left(-K_{diss} + \sqrt{K_{diss}^2 - 4K_{diss}[P_{total}](\Theta - 1)}\right)} + \Theta[P_{total}] \quad \text{Eq. 2}$$

Data were analyzed using Origin™ 7, using the one site bind function for nonlinear fit.

Isothermal Titration Calorimetry (ITC) of B-Raf Binding of Peptides

As confirmation of binding affinity in an alternate format and to investigate the thermodynamics of binding for peptides to B-Raf, ITC experiments were carried out for three peptides shown to interact with B-Raf through ITF measurements.

An isothermal titration calorimeter composed of two identical cells surrounded by an adiabatic jacket was used to perform ITC measurements. The thermopile/thermocouple circuits were used to detect temperature differences between a reference cell (filled with buffer or water) and a sample cell containing the macromolecule. During an experiment, ligand is titrated into the sample cell in precisely known aliquots, causing heat to be either taken up or evolved (depending on the nature of the reaction). Measurements consist of the time-dependent input of power required to maintain equal temperatures between the sample and reference cells. In an exothermic reaction, the temperature in the sample cell increases upon addition of ligand. This causes the feedback power to the sample cell to be decreased (remember: a reference power is applied to the reference cell) in order to maintain an equal temperature between the two cells. In an endothermic reaction, the opposite occurs; the feedback circuit increases the power in order to maintain a constant temperature (isothermic/isothermal operation). Observations are plotted as the power needed to maintain the reference and the sample cell at an identical temperature against time. As a result, the experimental raw data consists of a series of spikes of heat flow (power), with every spike corresponding to one ligand injection. These heat flow spikes/pulses are integrated with respect to time, giving the total heat exchanged per injection. The pattern of these heat effects as a function of the molar ratio [ligand]/[macromolecule] can then be analyzed to give the thermodynamic parameters of the interaction under study.

Peptide corresponding to SEQ ID NO: 8 (ITF $K_d$=2.8 μM) was measured by ITC ($K_d$=14.9±10.8 μM; ΔH=−34.8 kJ/mol; ΔS=−28.4 J/mol·K). Peptide 17 (ITF $K_d$=0.13 μM) measured by ITC $K_d$=0.35±0.17 μM. For a flexible linear peptide (also for 8) with high entropy in the free state, binding is primarily enthalpy driven (ΔH=−199 kJ/mol) and the entropy term is unfavorable for the overall free energy (ΔS=−567J/mol·K). The cyclic derivative, 36 was measured by ITC ($K_d$=0.31±0.16 μM) as compared with the ITF assay ($K_d$=0.46 μM). Binding of the macrocyclic peptide is driven more by entropic factors than enthalpic (ΔH=−9.41 kJ/mol and ΔS=92.05 J/mol·K).

Tissue Culture

The generation of MCF-10Atet cells, a subline of the human mammary epithelial cell line MCF-10A, was described previously. MCF-10Atet cells were grown at 37° C. in a water vapor saturated 5% $CO_2$ atmosphere in conventional tissue culture plastic vessels (Sarstedt, Nümbrecht, Germany) containing DMEM/F12 medium (PAN-Biotech GmbH, Aidenbach, Germany) supplemented with 5 vol % horse serum (PAA, Cölbe, Germany), 1 vol % glutamine (PAN-Biotech GmbH, Aidenbach, Germany), 1 vol % HEPES (PAN-Biotech GmbH, Aidenbach, Germany), 1 vol % penicillin/streptomycin (PAN-Biotech GmbH, Aidenbach, Germany), 250 μg hydrocortisone (Sigma-Aldrich, Munich, Germany), 50 μg choleratoxin (Sigma-Aldrich, Munich, Germany), 10 μg human recombinant epidermal growth factor (R&D Systems®, Wiesbaden-Nordenstadt, Germany), and 4.858 mg human recombinant insulin (Actrapid® Penfill® solution, Novo Nordisk Pharma GmbH, Mainz, Germany). Cells were passaged twice a week or upon reaching confluency and detached by trypsin/EDTA solution. Five hundred cells were plated onto 6 well plates and grown for 24 hours prior to peptide treatment.

Western Blotting $NRAS^{Q61K}$-mutant SBCl2 melanoma cells were electroporated with the BioRad Gene Pulser XCell™ in the presence of the indicated concentrations of peptide. Following recovery at 37° C. for 30 minutes, cells were treated with 1 μM PLX4032 for 1 hour or DMSO as a vehicle control. Subsequently, the cells were harvested, lysed using RIPA buffer, and analyzed by Western blotting using the indicated antibodies.

While certain embodiments of the disclosed subject matter have been described using specific terms, such description is for illustrative purposes only, and it is to be understood that changes and variations may be made without departing from the spirit or scope of the subject matter.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged in whole or in part. Furthermore, those of ordinary skill in the art will appreciate that the foregoing description is by way of example only and is not intended to limit the invention further described in the appended claims.

What is claimed is:

1. A peptide comprising no more than 19 amino acid residues, the peptide comprising a macrocycle including 5 or more amino acid residues in the ring structure of the macrocycle, the peptide comprising one of SEQ ID NO: 50 (VKRKTRHVNILLFMEY) or SEQ ID NO: 53 (VLRKKRHVNELLFMG).

2. The peptide of claim 1, the peptide comprising SEQ ID NO: 50, the macrocycle ring structure consisting of the amino acid residues from the first lysine to the glutamic acid of SEQ ID NO: 50.

3. The peptide of claim 1 consisting of SEQ ID NO: 50.

4. The peptide of claim 1, the peptide comprising SEQ ID NO: 53, the macrocycle ring structure consisting of the amino acid residues from the second lysine to the glutamic acid of SEQ ID NO: 53.

5. The peptide of claim 4 consisting of SEQ ID NO: 53.

6. The peptide of claim 1, the peptide comprising an N-terminal capping group and/or a C-terminal capping group.

7. The peptide of claim 1, wherein the peptide further comprises an N-methylation of a residue.

8. The peptide of claim 1, the peptide further comprising an N-terminal capping group and/or a C-terminal capping group.

9. The peptide of claim 8, wherein the N-terminal capping group and/or the C-terminal capping group are independently selected from Structure I:

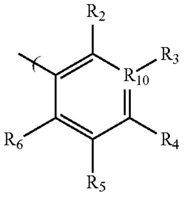

in which $R_2$-$R_6$ are independently selected from hydrogen, carboxyl, alkyl, alkyl ester, hydroxyl, methoxy, halogen, amino, alkylamino, thiol, thioalkylether, sulfonamide, phosphate, nitro, methylamine, or boronic acid, and $R_{10}$ is C or N, and $R_3$ is relevant only when $R_{10}$ is C;

Structure II:

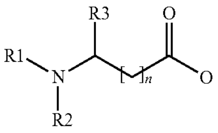

in which R1, R2, and R3 are selected from a hydrogen (H) or an alkyl group having a chain length of 1-3 carbons and n=0-3;

Structure III:

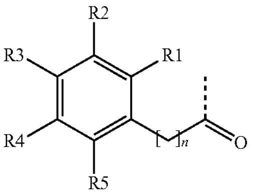

in which R1-R5 can be independently selected from a hydrogen (H) a linear or branched alkyl group having a chain length of 1-5 carbons, an amine, aminoalkyl, thiol, thioalkylether, an amide, a carboxylate, a sulfate, a sulfamide, a cyano, or a halogen, and n=0-4;

Structure IV:

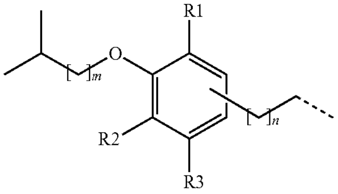

in which R1-R3 can be independently selected from a hydrogen (H) a linear or branched alkyl group having a chain length of 1-5 carbons, an amine, an amide, a carboxylate, a sulfate, a sulfamide, a cyano, or a halogen; and the alkyl chain having a chain length, n=0-3, may be positioned on the phenyl ring at any position including ortho, meta, or para, relative to the alkoxy group having a chain length, m=1-5; and Structure V:

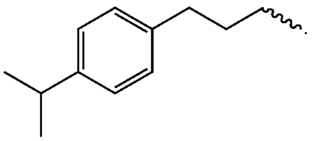

10. The peptide of claim 8, wherein the N-terminal capping group is selected from the group consisting of:

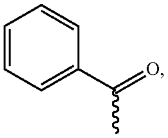 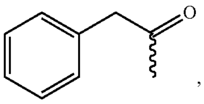, 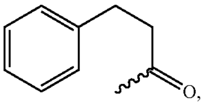 and 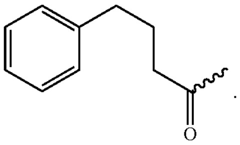.

11. The peptide of claim 8, wherein the C-terminal capping group is selected from the group consisting of:

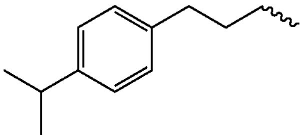,

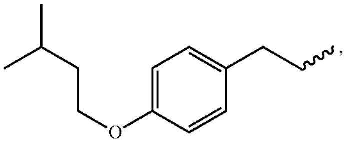,

-continued

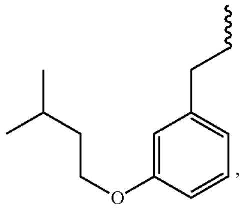

, and

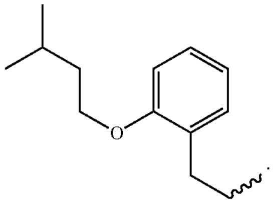

.

12. A peptide comprising no more than 19 amino acid residues, the peptide comprising a sequence of Lysine-N-methylated arginine-octyl-Glutamic Acid (K-MeR-octyl-E).

13. The peptide of claim 12, the amino acid residues of the peptide consisting of SEQ ID NO: 65.

14. A peptide comprising no more than 19 amino acid residues, the peptide comprising:

a macrocycle consisting of six amino acid residues in the ring structure of the macrocycle, the peptide comprising SEQ ID NO: 61 (KRHPAELLFMG) or a sequence comprising Lysine-N-methylated arginine-D-alanine-Proline-Alanine-Glutamic Acid (K-MeR-a-PAE).

15. The peptide of claim 14, the amino acid residues of the peptide comprises SEQ ID NO: 61.

16. The peptide of claim 14, the amino acid residues of the peptide comprises K-MeR-a-PAE.

17. The peptide of claim 14, the peptide further comprising a linear peptide portion.

18. The peptide of claim 17, wherein the linear peptide portion comprises one or more of the modifications of SEQ ID NO: 1.

19. The peptide of claim 18, wherein the modifications comprise N-methylation of a residue of SEQ ID NO: 1.

* * * * *